United States Patent
Sohum et al.

(10) Patent No.: US 12,236,377 B2
(45) Date of Patent: Feb. 25, 2025

(54) METHOD AND SYSTEM FOR SWITCHING AND HANDOVER BETWEEN ONE OR MORE INTELLIGENT CONVERSATIONAL AGENTS

(71) Applicant: Affle International Pte. Ltd., Singapore (SG)

(72) Inventors: Anuj Khanna Sohum, Singapore (SG); Charles Yong Jien Foong, Singapore (SG); Madhusudana Ramakrishna, Sinapore (SG)

(73) Assignee: Affle International Pte. Ltd., Singapore (SG)

( * ) Notice: Subject to any disclaimer, the term of this patent is extended or adjusted under 35 U.S.C. 154(b) by 51 days.

(21) Appl. No.: 17/073,274

(22) Filed: Oct. 16, 2020

(65) Prior Publication Data
US 2021/0117893 A1 Apr. 22, 2021

(30) Foreign Application Priority Data
Oct. 18, 2019 (SG) .............................. 10201909738T

(51) Int. Cl.
*G06Q 30/00* (2023.01)
*G06F 16/245* (2019.01)
(Continued)

(52) U.S. Cl.
CPC ..... *G06Q 10/06315* (2013.01); *G06F 16/245* (2019.01); *G06F 40/237* (2020.01);
(Continued)

(58) Field of Classification Search
CPC ....... G06Q 10/06315; G06Q 10/06395; G06Q 20/123; G06Q 20/127; G06Q 30/016;
(Continued)

(56) References Cited

U.S. PATENT DOCUMENTS

| | | | |
|---|---|---|---|
| 2019/0121850 A1* | 4/2019 | Banerjee | H04L 67/36 |
| 2019/0124020 A1* | 4/2019 | Bobbarjung | G06F 16/958 |
| 2020/0252205 A1* | 8/2020 | Padmanabhan | H04L 9/0643 |

FOREIGN PATENT DOCUMENTS

WO WO-2020219203 A1 * 10/2020 ............ G06F 11/322

OTHER PUBLICATIONS

Cui et al., AI and Procurement, https://www.researchgate.net/profile/Meng-Li-208/publication/353820579_AI_and_Procurement/links/6140cee1dabce51cf451e9a3/AI-and-Procurement.pdf, Manufacturing & Service Operations Management, 2020 (Year: 2020).*

* cited by examiner

*Primary Examiner* — Crystol Stewart
*Assistant Examiner* — Uche Byrd
(74) *Attorney, Agent, or Firm* — Kolisch Hartwell, P.C.

(57) ABSTRACT

The present disclosure provides a method and system to perform switching and handover between one or more intelligent conversational agents. The system receives a first set of data in real-time. The system collects a second set of data in real-time. The system fetches one or more queries from a plurality of users for a mega bot. The system analyses the first set of data, the second set of data and the one or more queries using one or more machine learning algorithms. The system selects a suitable intelligent conversational agent from the one or more intelligent conversational agents having a trust score above a threshold level. The system switches between the one or more intelligent conversational agents in the mega bot interacting with the plurality of users based on a plurality of aspects of corresponding query of the one or more queries and a plurality of factors.

19 Claims, 7 Drawing Sheets

(51) Int. Cl.
*G06F 40/237* (2020.01)
*G06F 40/30* (2020.01)
*G06N 5/043* (2023.01)
*G06N 20/00* (2019.01)
*G06Q 10/0631* (2023.01)
*G06Q 10/0639* (2023.01)
*G06Q 20/12* (2012.01)
*G06Q 30/016* (2023.01)
*G06Q 30/0201* (2023.01)
*G06Q 30/0601* (2023.01)
*H04L 51/02* (2022.01)
*G06Q 40/03* (2023.01)
*G06Q 40/06* (2012.01)
*G06Q 40/08* (2012.01)
*G06Q 50/14* (2012.01)
*G06Q 50/16* (2012.01)
*G06Q 50/20* (2012.01)
*G16H 10/20* (2018.01)
*G16H 40/20* (2018.01)

(52) U.S. Cl.
CPC .............. *G06F 40/30* (2020.01); *G06N 5/043* (2013.01); *G06N 20/00* (2019.01); *G06Q 10/06395* (2013.01); *G06Q 20/123* (2013.01); *G06Q 20/127* (2013.01); *G06Q 30/016* (2013.01); *G06Q 30/0201* (2013.01); *G06Q 30/0609* (2013.01); *G06Q 30/0613* (2013.01); *H04L 51/02* (2013.01); *G06Q 30/0633* (2013.01); *G06Q 40/03* (2023.01); *G06Q 40/06* (2013.01); *G06Q 40/08* (2013.01); *G06Q 50/14* (2013.01); *G06Q 50/16* (2013.01); *G06Q 50/205* (2013.01); *G16H 10/20* (2018.01); *G16H 40/20* (2018.01)

(58) Field of Classification Search
CPC ........... G06Q 30/0201; G06Q 30/0609; G06Q 30/0613; G06Q 30/0633; G06Q 40/025; G06Q 40/06; G06Q 40/08; G06Q 50/14; G06Q 50/16; G06Q 50/205; G06F 16/245; G06F 40/237; G06F 40/30; G06N 20/00; G06N 5/043; H04L 51/02; G16H 40/20; G16H 10/20
See application file for complete search history.

METHOD AND SYSTEM FOR SWITCHING AND HANDOVER BETWEEN ONE OR MORE INTELLIGENT CONVERSATIONAL AGENTS

TECHNICAL FIELD

The present disclosure relates to the field of agents (i.e. chatbots), and in particular, relates to method and system for switching and handover between one or more intelligent conversational agents (chatbots).

INTRODUCTION

Now a days, agents (say chatbots, conversational agents, virtual reality/augmented reality engagements) are becoming increasingly popular as an interesting and interactive medium for the provision of information. For example, a chatbot may replace a text based FAQ facility. Generally, FAQ facilities provide a list of frequently asked questions. Further, a user selects one of the questions from the list. Furthermore, the user is automatically presented an answer to the question. Generally, chatbots provide a conversational experience for interaction with the user. The user may ask a question and the chatbot attempts to interpret the question, and then provide an answer. Conventionally, the chatbots are not deployed by a single vendor. Moreover, different vendors create and provide support for different chatbots. Also, it becomes very difficult to use different chatbots without ripping out information and provide solutions to the user based on different queries of the user.

SUMMARY

In a first example, a computer-implemented method is provided. The computer-implemented method to switch and handover between one or more intelligent conversational agents. The computer-implemented method includes a first step to receive a first set of data in real-time at a chatbot switching system with a processor. The first set of data is associated with a plurality of users. The first set of data includes user behavioral information, past engagements with conversational agents and user profile information. In addition, the computer-implemented method includes a second step to collect a second set of data in real-time at the chatbot switching system with the processor. The second set of data is associated with the one or more intelligent conversational agents. The second set of data includes a trust score associated with each of the one or more intelligent conversational agents, and confidence level of the one or more intelligent conversational agents. The second set of data includes past performance of the one or more intelligent conversational agents, and performance of each of the one or more intelligent conversational agents in a virtual environment. Further, the computer-implemented method includes a third step to fetch one or more queries from the plurality of users for a mega bot at the chatbot switching system with the processor. The one or more queries are associated to a scope of field. Each of the one or more queries has a plurality of aspects. The plurality of aspects includes context, linguistic style, sentence construction, and lexical ambiguity. Furthermore, the computer-implemented method includes a fourth step to analyze the first set of data, the second set of data and the one or more queries using one or more machine learning algorithms at the chatbot switching system with the processor. The analysis is performed based on training of a machine learning model. The analysis is performed to enable selection of a suitable intelligent conversational agent from the one or more intelligent conversational agents. The analysis is performed in real time. Moreover, the computer-implemented method includes a fifth step to select the suitable intelligent conversational agent from the one or more intelligent conversational agents having the trust score above a threshold level according to the plurality of aspects of each of the one or more queries. The selection is based on the plurality of factors and the analysis of the first set of data, the second set of data and the one or more queries. The mega bot selects the suitable intelligent conversational agent from the one or more intelligent conversational agents. The threshold level is defined by an enterprise. The plurality of factors includes identification of the plurality of aspects, confidence level of the one or more intelligent conversational agents, and past performance of the one or more intelligent conversational agents. The plurality of factors includes behavior identification of the plurality of users, and automated testing performance of the one or more intelligent conversational agents. The plurality of factors includes performance of each of the one or more intelligent conversational agents in the virtual environment, cost of engagement with the one or more intelligent conversational agents and a feedback from the plurality of users. Also, the computer-implemented method includes a sixth step to switch between the one or more intelligent conversational agents in the mega bot interacting with the plurality of users based on the plurality of aspects of corresponding query of the one or more queries and the plurality of factors.

In an embodiment of the present disclosure, the computer-implemented method includes creation of an online chatbot marketplace to enable one or more vendors to upload the one or more intelligent conversational agents. In addition, the computer-implemented method enables the enterprise to access the one or more intelligent conversational agents from the one or more vendors. Further, each of the one or more intelligent conversational agents is affiliated with the scope of field.

In an embodiment of the present disclosure, the computer-implemented method enables integration of the one or more intelligent conversational agents to generate the mega bot in real-time. In addition, each of the one or more intelligent conversational agents has the trust score. Further, the trust score is dependent on the plurality of factors associated with the one or more intelligent conversational agents.

In an embodiment of the present disclosure, the computer-implemented method includes computation of the trust score for each of the one or more intelligent conversational agents uploaded on the online chatbot marketplace by the one or more vendors. In addition, the computer-implemented method ranks each of the one or more intelligent conversational agents in the online chatbot marketplace based on the trust score.

In an embodiment of the present disclosure, the computer-implemented method receives the confidence level of the one or more intelligent conversational agents for responding to the one or more queries of the plurality of users. In addition, each of the one or more intelligent conversational agents claims to have the confidence level to create response for the one or more queries.

In an embodiment of the present disclosure, the computer-implemented method includes normalization of the trust score of each of the one or more intelligent conversational agents based on each of the plurality of factors.

In an embodiment of the present disclosure, the computer-implemented method includes prediction of journey of conversation between the plurality of users and the mega bot based on analysis performed on the first set of data, the second set of data, and the one or more queries using the one or more machine learning algorithms.

In an embodiment of the present disclosure, the computer-implemented method includes detection of the plurality of aspects associated with the one or more queries using the machine learning model in real-time.

In an embodiment of the present disclosure, the computer-implemented method includes determination of transition of the plurality of aspects within the conversation based on analysis performed on the one or more queries using the one or more machine learning algorithms. In addition, the determination of the transition of the plurality of aspects within the conversation enables the chatbot switching system to switch between the one or more intelligent conversational agents in the mega bot.

In a second example, a computer system is provided. The computer system includes one or more processors, a signal generator circuitry embedded inside a computing device for generating a signal, and a memory. The memory is coupled to the one or more processors. The memory stores instructions. The instructions are executed by the one or more processors. The execution of the instructions causes the one or more processors to perform a method to switch and handover between the one or more intelligent conversational agents. The method includes a first step to receive the first set of data in real-time at the chatbot switching system. The first set of data is associated with the plurality of users. The first set of data includes user behavioral information, past engagements with conversational agents and user profile information. In addition, the method includes a second step to collect the second set of data in real-time at the chatbot switching system. The second set of data is associated with the one or more intelligent conversational agents. The second set of data includes the trust score associated with each of the one or more intelligent conversational agents, and confidence level of the one or more intelligent conversational agents. The second set of data includes past performance of the one or more intelligent conversational agents, and performance of each of the one or more intelligent conversational agents in the virtual environment. Further, the method includes a third step to fetch the one or more queries from the plurality of users for the mega bot at the chatbot switching system. The one or more queries are associated to the scope of field. Each of the one or more queries has the plurality of aspects. The plurality of aspects includes context, linguistic style, sentence construction, and lexical ambiguity. Furthermore, the method includes a fourth step to analyze the first set of data, the second set of data and the one or more queries using the one or more machine learning algorithms at the chatbot switching system. The analysis is performed based on training of the machine learning model. The analysis is performed to enable selection of the suitable intelligent conversational agent from the one or more intelligent conversational agents. The analysis is performed in real time. Moreover, the method includes a fifth step to select the suitable intelligent conversational agent from the one or more intelligent conversational agents having the trust score above the threshold level according to the plurality of aspects of each of the one or more queries. The selection is based on the plurality of factors and the analysis of the first set of data, the second set of data and the one or more queries. The mega bot selects the suitable intelligent conversational agent from the one or more intelligent conversational agents. The threshold level is defined by the enterprise. The plurality of factors includes identification of the plurality of aspects, confidence level of the one or more intelligent conversational agents, and past performance of the one or more intelligent conversational agents. The plurality of factors includes behavior identification of the plurality of users, and automated testing performance of the one or more intelligent conversational agents. The plurality of factors includes performance of each of the one or more intelligent conversational agents in the virtual environment, cost of engagement with the one or more intelligent conversational agents and the feedback from the plurality of users. Also, the method includes a sixth step to switch between the one or more intelligent conversational agents in the mega bot interacting with the plurality of users based on the plurality of aspects of corresponding query of the one or more queries and the plurality of factors.

In a third example, a non-transitory computer readable medium is provided. The non-transitory computer readable medium encodes computer executable instructions that, when executed by at least one processor, performs a method to switch and handover between the one or more intelligent conversational agents. The method includes a first step to receive the first set of data in real-time. The first set of data is associated with the plurality of users. The first set of data includes user behavioral information, past engagements with conversational agents and user profile information. In addition, the method includes a second step to collect the second set of data in real-time. The second set of data is associated with the one or more intelligent conversational agents. The second set of data includes the trust score associated with each of the one or more intelligent conversational agents, and confidence level of the one or more intelligent conversational agents. The second set of data includes past performance of the one or more intelligent conversational agents, and performance of each of the one or more intelligent conversational agents in the virtual environment. Further, the method includes a third step to fetch the one or more queries from the plurality of users for the mega bot. The one or more queries are associated to the scope of field. Each of the one or more queries has the plurality of aspects. The plurality of aspects includes context, linguistic style, sentence construction, and lexical ambiguity. Furthermore, the method includes a fourth step to analyze the first set of data, the second set of data and the one or more queries using the one or more machine learning algorithms. The analysis is performed based on training of the machine learning model. The analysis is performed to enable selection of the suitable intelligent conversational agent from the one or more intelligent conversational agents. The analysis is performed in real time. Moreover, the method includes a fifth step to select the suitable intelligent conversational agent from the one or more intelligent conversational agents having the trust score above the threshold level according to the plurality of aspects of each of the one or more queries. The selection is based on the plurality of factors and the analysis of the first set of data, the second set of data and the one or more queries. The mega bot selects the suitable intelligent conversational agent from the one or more intelligent conversational agents. The threshold level is defined by the enterprise. The plurality of factors includes identification of the plurality of aspects, confidence level of the one or more intelligent conversational agents, and past performance of the one or more intelligent conversational agents. The plurality of factors includes behavior identification of the plurality of users, and automated testing performance of the one or more intelligent conversational agents. The plurality of factors includes performance of each of the one or more intelligent conversational agents in the virtual environment, cost of engagement with the one or more intelligent conversational agents and the feedback from the plurality of users. Also, the method includes a sixth step to switch between the one or more intelligent conversational agents in the mega bot interacting with the plurality of users based on the plurality of aspects of corresponding query of the one or more queries and the plurality of factors.

BRIEF DESCRIPTION OF THE DRAWINGS

Figure 1:
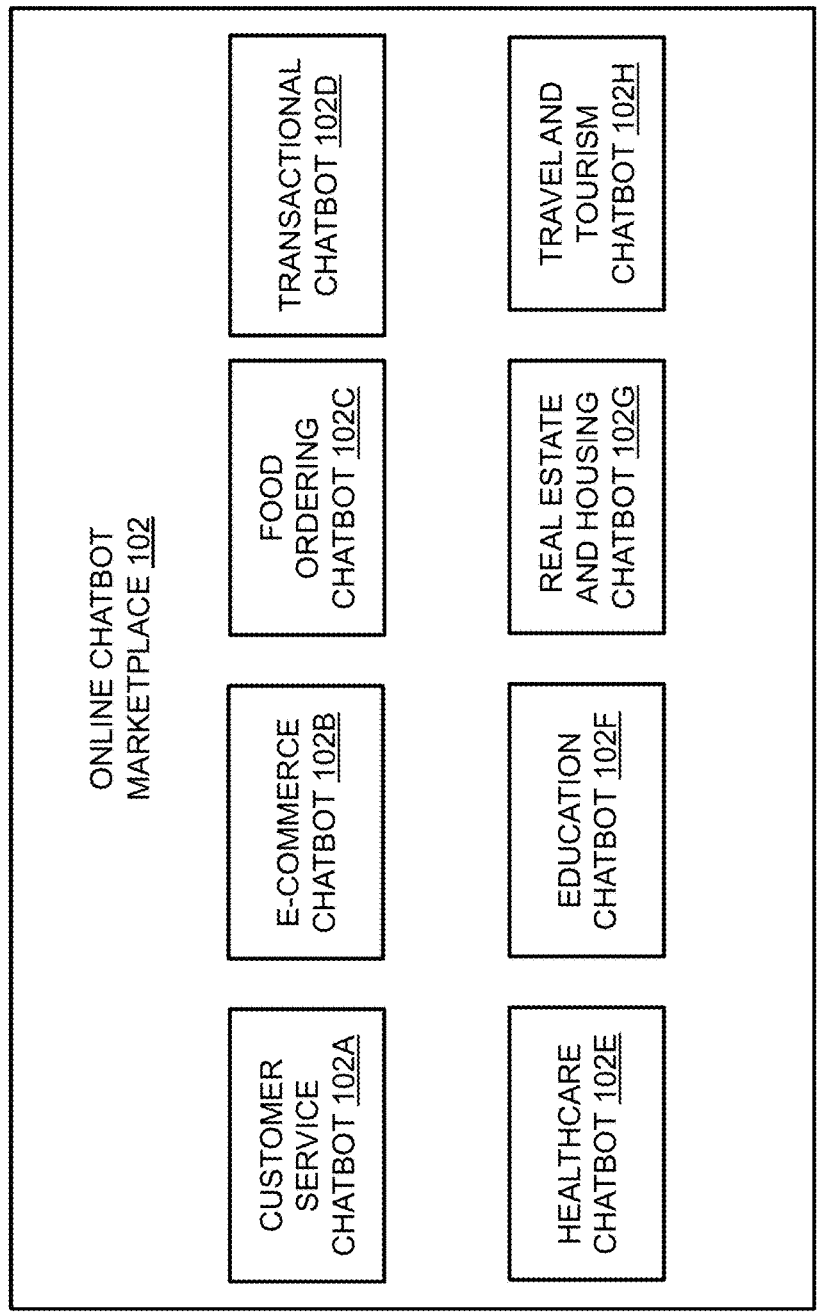
Figure 2:
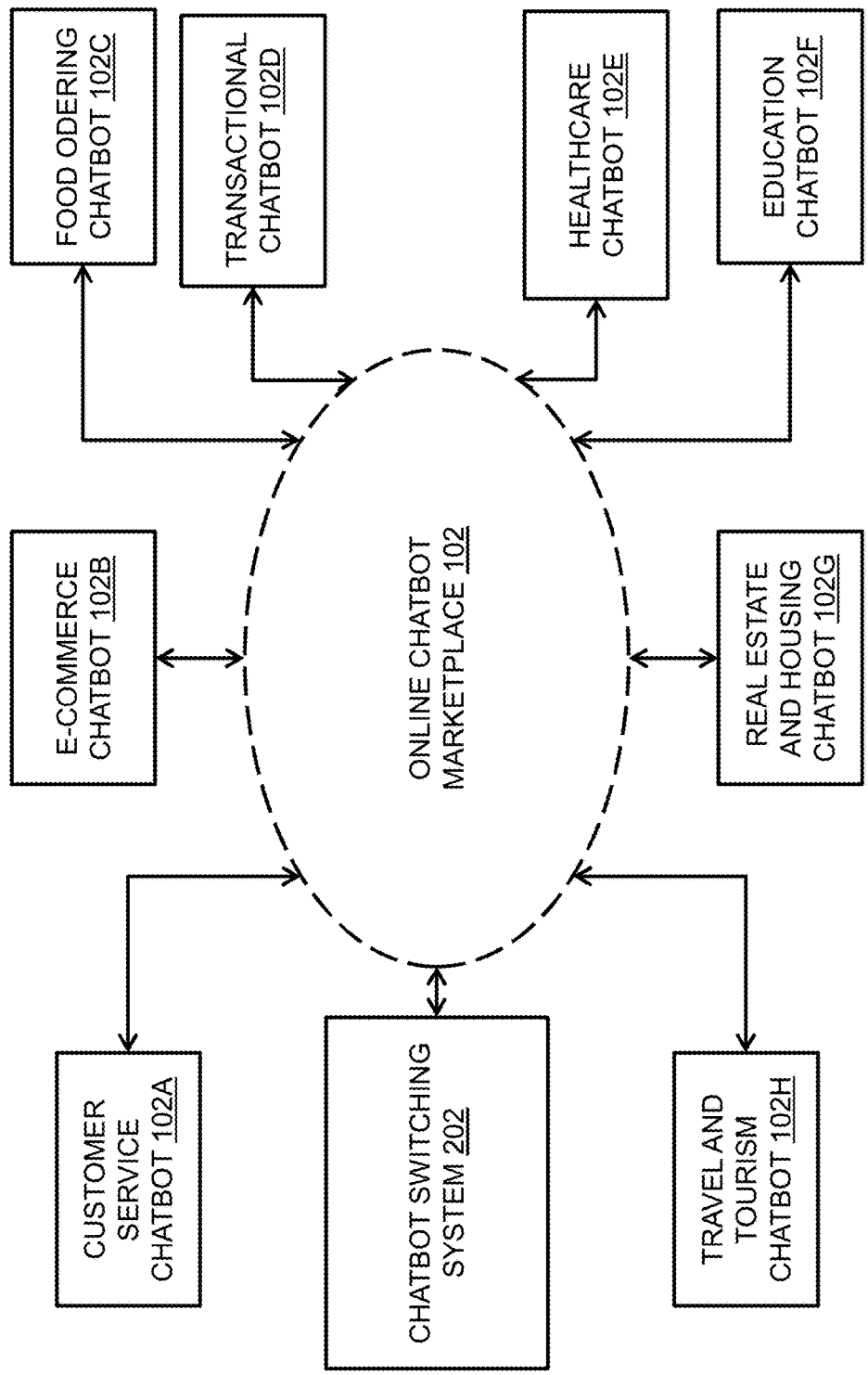
Figure 3:
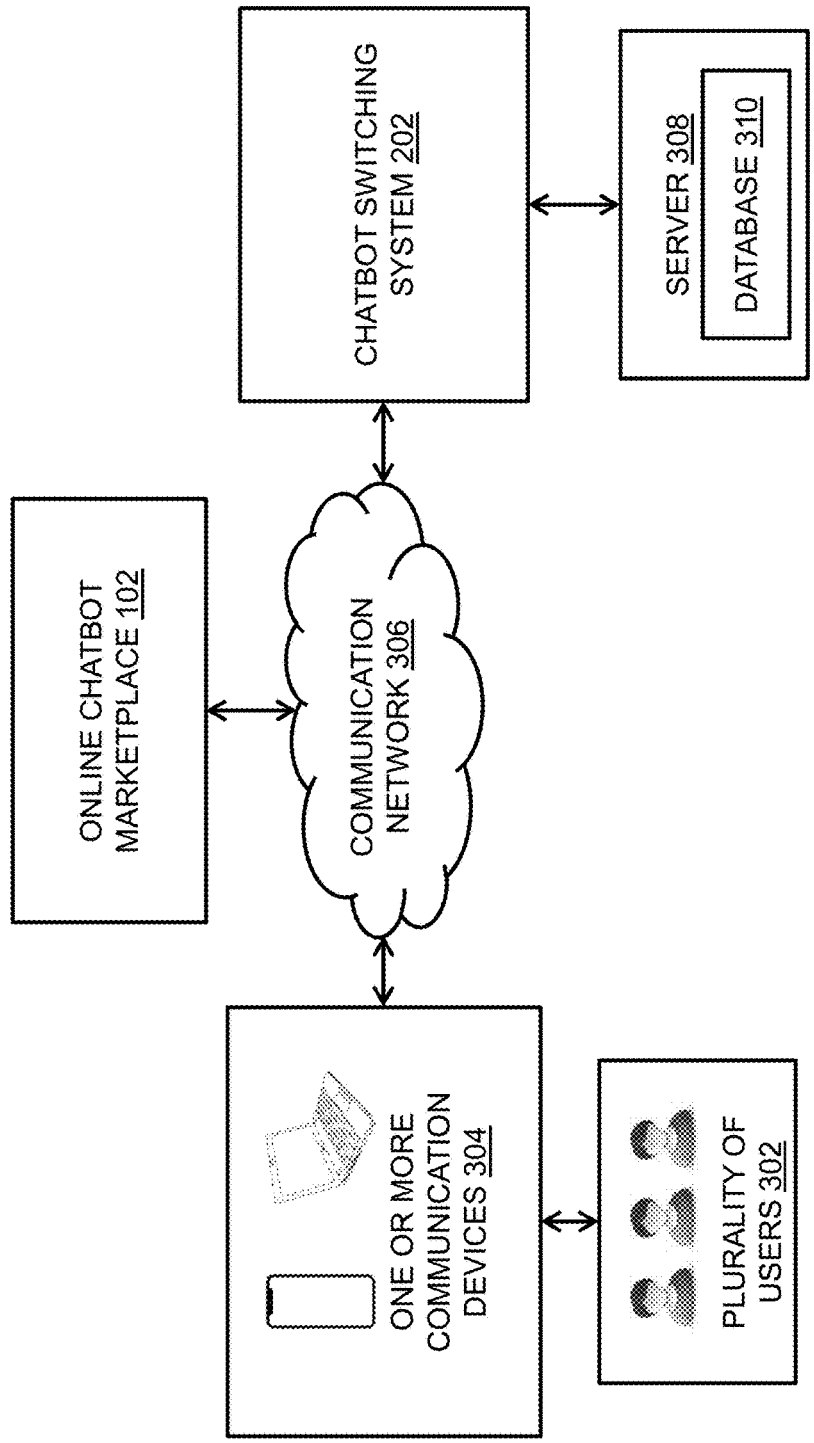
Figure 4:
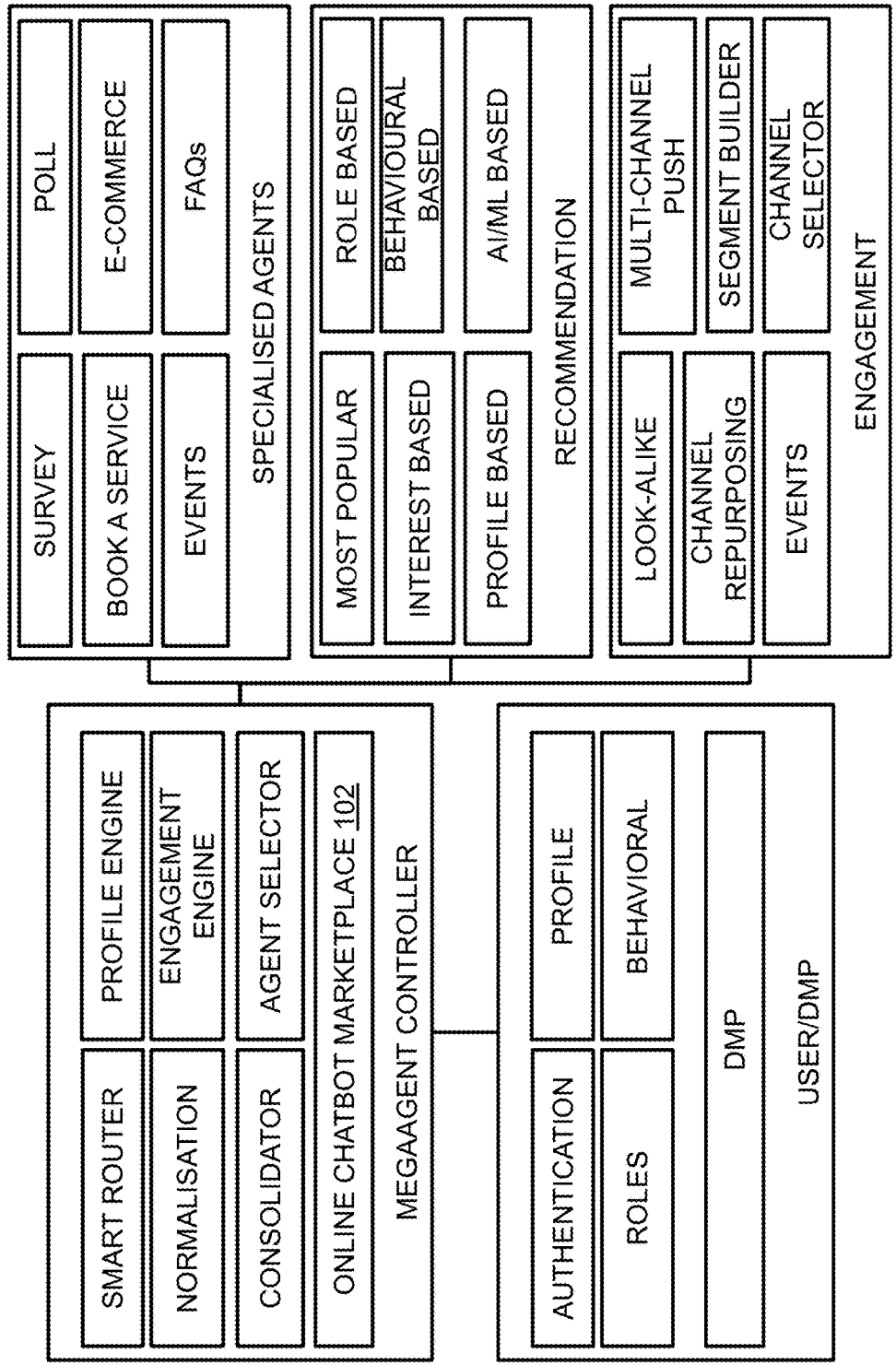
Figure 5A:
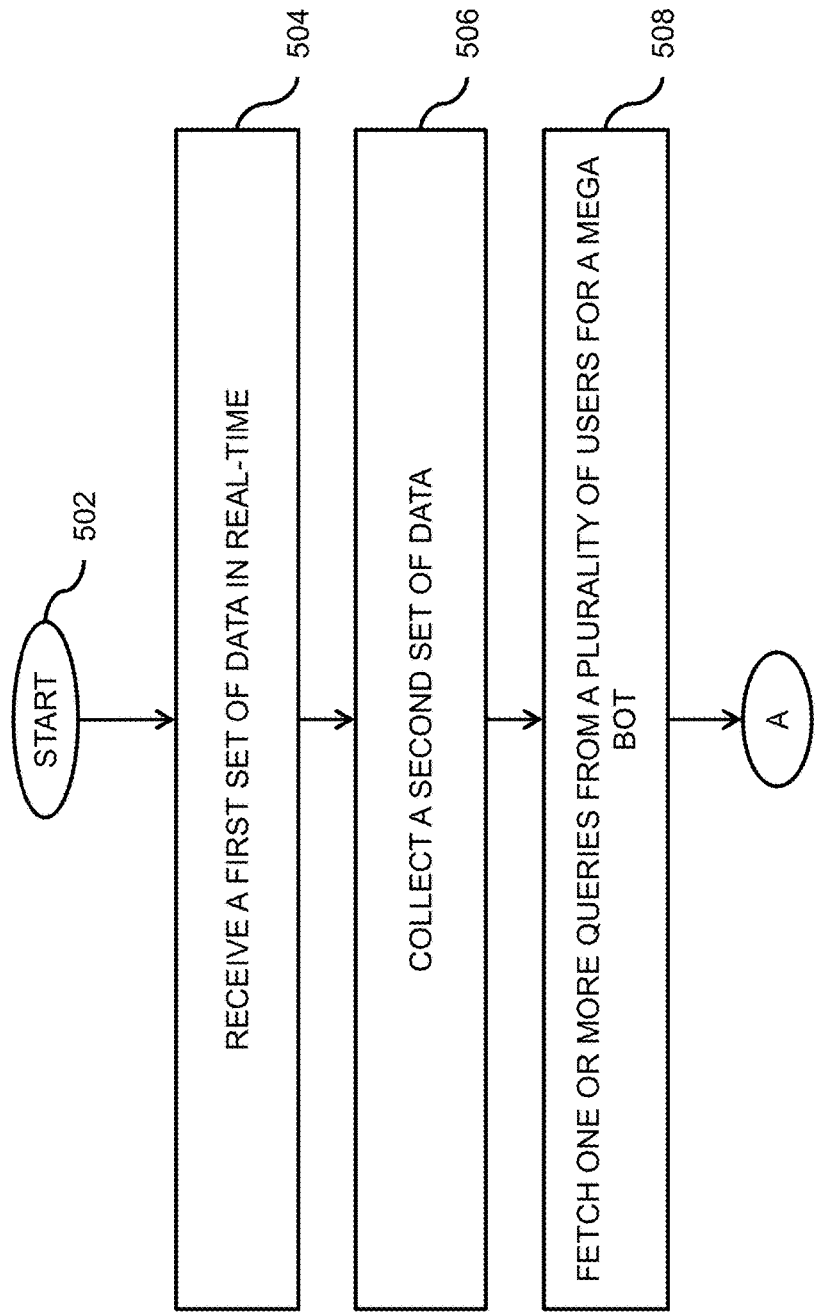
Figure 5B:
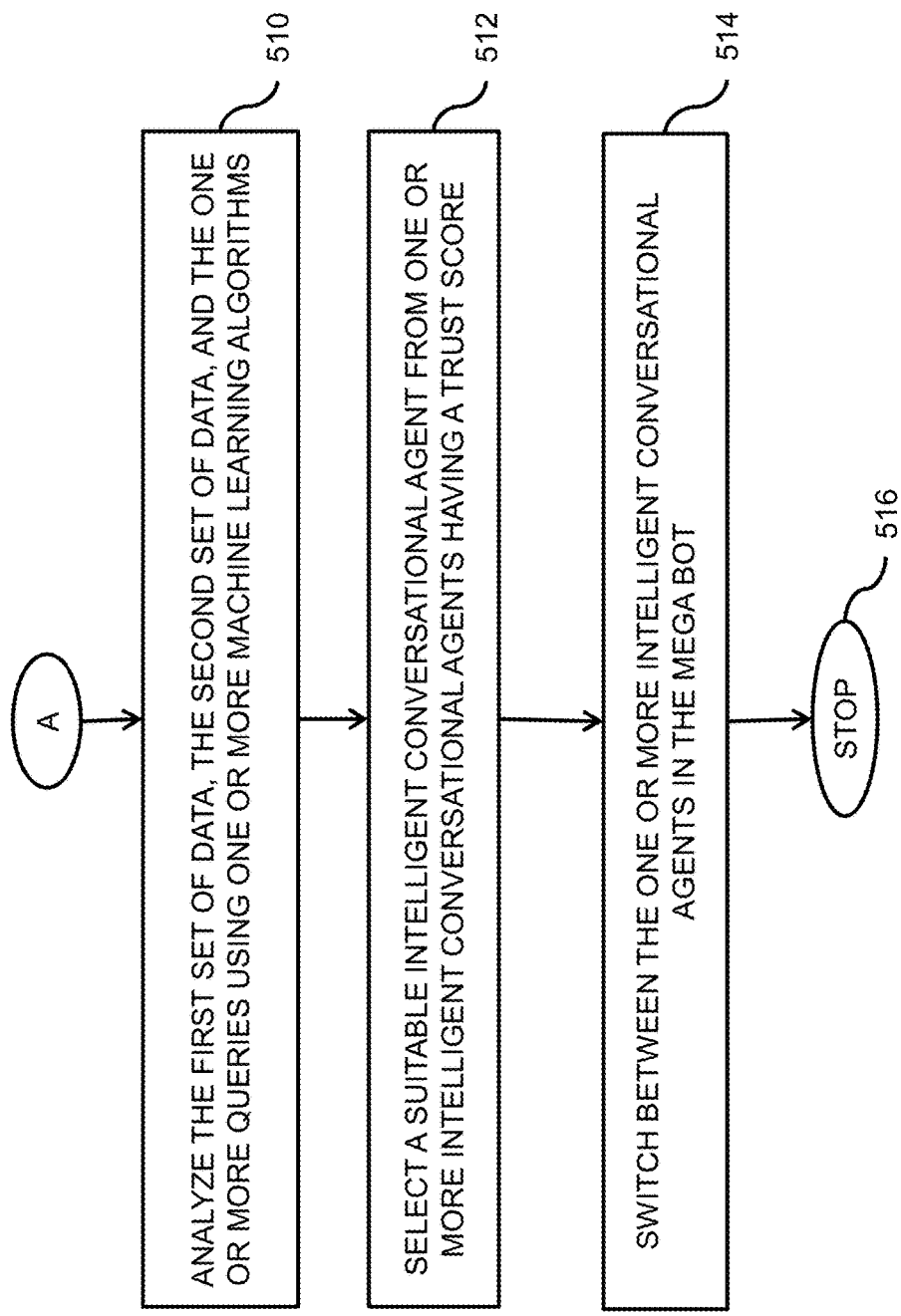
Figure 6:
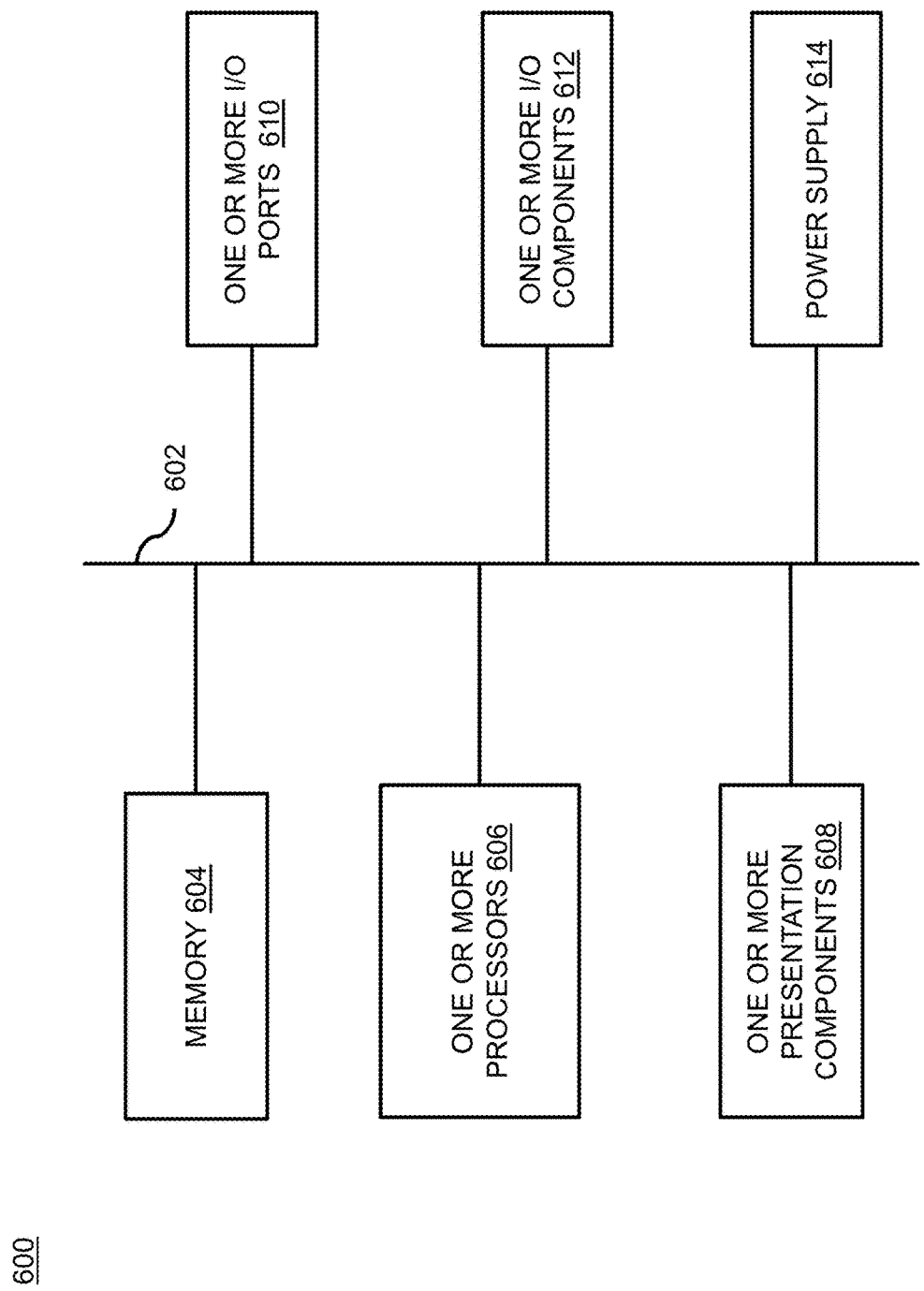

Having thus described the invention in general terms, references will now be made to the accompanying figures, wherein:

FIG. 1 illustrates a block diagram of an online chatbot marketplace, in accordance with various embodiments of the present disclosure;

FIG. 2 illustrates a general overview of a chatbot switching system having the online chatbot marketplace, in accordance with various embodiments of the present disclosure;

FIG. 3 illustrates an interactive computing environment for switching and handover between one or more intelligent conversational agents, in accordance with various embodiments of the present disclosure;

FIG. 4 illustrates a general overview of the chatbot switching system, in accordance with various embodiments of the present invention;

FIGS. 5A and 5B illustrate a flowchart of a method for switching and handover between the one or more intelligent conversational agents, in accordance with various embodiments of the present disclosure; and FIG. 6 illustrates a block diagram of a computing device, in accordance with various embodiments of the present invention.

It should be noted that the accompanying figures are intended to present illustrations of exemplary embodiments of the present disclosure. These figures are not intended to limit the scope of the present disclosure. It should also be noted that accompanying figures are not necessarily drawn to scale.

DETAILED DESCRIPTION

In the following description, for purposes of explanation, numerous specific details are set forth in order to provide a thorough understanding of the present technology. It will be apparent, however, to one skilled in the art that the present technology can be practiced without these specific details. In other instances, structures and devices are shown in block diagram form only in order to avoid obscuring the present technology.

Reference in this specification to "one embodiment" or "an embodiment" means that a particular feature, structure, or characteristic described in connection with the embodiment is included in at least one embodiment of the present technology. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Reference will now be made in detail to selected embodiments of the present disclosure in conjunction with accompanying figures. The embodiments described herein are not intended to limit the scope of the disclosure, and the present disclosure should not be construed as limited to the embodiments described. This disclosure may be embodied in different forms without departing from the scope and spirit of the disclosure. It should be understood that the accompanying figures are intended and provided to illustrate embodiments of the disclosure described below and are not necessarily drawn to scale. In the drawings, like numbers refer to like elements throughout, and thicknesses and dimensions of some components may be exaggerated for providing better clarity and ease of understanding.

It should be noted that the terms "first", "second", and the like, herein do not denote any order, quantity, or importance, but rather are used to distinguish one element from another. Further, the terms "a" and "an" herein do not denote a limitation of quantity, but rather denote the presence of at least one of the referenced items.

FIG. 1 illustrates a block diagram 100 of an online chatbot marketplace 102, in accordance with various embodiments of the present disclosure. In general, marketplace corresponds to a platform that enables various individuals to obtain, upload and access valuable resources or services. The online chatbot marketplace 102 includes one or more intelligent conversational agents. Each of the one or more intelligent conversational agents is affiliated with a scope of field. In addition, the one or more intelligent conversational agents include a customer service chatbot 102A, an e-commerce chatbot 102B, a food ordering chatbot 102C, a transactional chatbot 102D, and a healthcare chatbot 102E. Further, the one or more intelligent conversational agents include an education platform 102F, a real estate and housing chatbot 102G, and a travel and tourism chatbot 102H. However, the one or more intelligent conversational agents are not limited to the above-mentioned conversational agents.

In an embodiment of the present disclosure, the one or more intelligent conversational agents are chatbots. In another embodiment of the present disclosure, the one or more intelligent conversational agents are video bots. In yet another embodiment of the present disclosure, the one or more intelligent conversational agents are personalized virtual assistants. In yet another embodiment of the present disclosure, the one or more intelligent conversational agents are any suitable conversational agents.

In an embodiment of the present disclosure, the one or more intelligent conversational agents include the customer service chatbot 102A. In general, customer service chatbot provides a conversational support for servicing to customers. In addition, the customer service chatbot 102A has the scope of field of customer support. In an example, an individual I interacts with a customer service chatbot C1 regarding servicing of a smart television using on a communication device D1 (let's say a smartphone).

In an embodiment of the present disclosure, the one or more intelligent conversational agents include the e-commerce chatbot 102B. In general, the e-commerce chatbot provides the conversational support to the customers for purchasing from online store. In addition, the e-commerce chatbot 102B has the scope of field of e-commerce. In an example, an Individual I requests to buy a plurality of products on an e-commerce chatbot C1 on a communication device D1 (let's say a desktop). In addition, the plurality of products include but may not be limited to laptops, tablets, mobiles, clocks, decorative accessories, books, home appliances, shoes, bags, jewelry, clothes, stationery, golf kit, and baseball bat.

In an embodiment of the present disclosure, the one or more intelligent conversational agents include the food ordering chatbot 102C. In general, food ordering chatbot provides the conversational support to the customers for ordering food online. In addition, the food ordering chatbot 102C has the scope of field of food. In an example, an individual I searches for chef's special menu on a food ordering chatbot C1 using a communication device D1 (let's say a laptop).

In an embodiment of the present disclosure, the one or more intelligent conversational agents include the transactional chatbot 102D. In general, transactional chatbot provides the conversational support to the customers to make transactions. In addition, the transactional chatbot 102D has the scope of field of finance. In an example, an individual I requests to initiate a plurality of financial services on a transactional chatbot C1 on a communication device D1 (let's say a desktop). In addition, the plurality of financial services include but may not be limited to online payments, car buying loans, house buying loans, credit cards, net banking, commercial banking, opening saving accounts, home equity, and stock exchange investment.

In an embodiment of the present disclosure, the one or more intelligent conversational agents include the healthcare chatbot 102E. In general, health chatbot provides the conversational support to the customers for healthcare services. In addition, the healthcare chatbot 102E has the scope of field of health services. In an example, an individual I requests for a plurality of health services on a healthcare chatbot C1 on a communication device D1 (let's say a tablet). In addition, the plurality of health services include but may not be limited to diet plans, medicines, physician clinics, nearest hospital, nearest fitness clubs, exercises, yoga classes, aerobics, healthy food orders, and medical tests.

In an embodiment of the present disclosure, the one or more intelligent conversational agents include the education chatbot 102F. In general, education chatbot provides the conversational support to the customers for educational services. In addition, the education chatbot 102F has the scope of field of education. In an example, a student S1 finds difficult to solve an integration problem I1. The student S1 requests for a plurality of educational services on an education chatbot C1 on a communication device D1 (let's say a smartphone). In addition, the plurality of educational services include but may not be limited to live teacher-student interaction, online subject wise informative media contents, entrance examination preparatory matters, and technical support for educational projects. However, the plurality of educational services is not limited to the above-mentioned services.

In an embodiment of the present disclosure, the one or more intelligent conversational agents include the real estate and housing chatbot 102G. In general, real estate and housing chatbot provides the conversational support to the customers for real estate services. In addition, the real estate and housing chatbot 102G has the scope of field of housing and real estate. In an example, an individual I requests for a plurality of real estate services on a real estate chatbot C1 through a communication device D2 (let's say a laptop). In addition, the plurality of real estate services include but may not be limited to houses on rent, properties on sale, house cleaning, garbage disposal, home repair, maintenance, and interior designing. However, the plurality of real estate services is not limited to the above-mentioned services.

In an embodiment of the present disclosure, the one or more intelligent conversational agents include the travel and tourism chatbot 102H. In general, travel and tourism chatbot provides the conversational support to the customers for travel and tourism services. In addition, the travel and tourism chatbot 102H has the scope of field of travel and tourism. In an example, an individual I requests for a plurality of travel services on a travel and tourism chatbot C1 through a communication device D1 (let's say a workstation). In addition, the plurality of travel services include but may not be limited to flight booking, train booking, taxi hiring, vacation deals, hotel booking, travel destination information, couch-surfing travel, and hot restaurant deals. However, the plurality of travel services is not limited to the above-mentioned services.

FIG. 2 illustrates a general overview 200 of a chatbot switching system 202 having the online chatbot marketplace 102, in accordance with various embodiments of the present disclosure. In an embodiment of the present disclosure, the chatbot switching system 202 categorizes each of the one or more intelligent conversational agents of the online chatbot marketplace 102 into one or more levels of a plurality of categories. In addition, the plurality of categories include but may not be limited to trusted conversational agents, untrusted conversational agents, and the scope of field. Further, the scope of field include but may not be limited to customer support, e-commerce, food, housing and real estate, finance, travel and tourism, health services, and education.

The chatbot switching system 202 creates the online chatbot marketplace 102 to enable one or more vendors to upload the one or more intelligent conversational agents. In addition, the online chatbot marketplace enables an enterprise to access the one or more intelligent conversational agents from the one or more vendors at same time. Further, each of the one or more intelligent conversational agents is affiliated with the scope of field. Furthermore, the one or more intelligent conversational agents include the customer service chatbot 102A, the e-commerce chatbot 102B, the food ordering chatbot 102C, the transactional chatbot 102D, and the healthcare chatbot 102E. Further, the one or more intelligent conversational agents include the education platform 102F, the real estate and housing chatbot 102G, and the travel and tourism chatbot 102H.

The chatbot switching system 202 categorizes the customer service chatbot 102A into the one or more levels of the scope of field of customer support. In addition, the one or more levels of the scope of field of customer support include but may not be limited to laptop services, air-conditioning services, microwave services, refrigerator services, washing machine services, and water purifier services. Further, the one or more levels of the scope of field of customer support include but may not be limited to chimney services, geyser services, air cooler services, and television services. However, the one or more levels of the scope of field of customer support are not limited to the above-mentioned services. In an embodiment of the present disclosure, each of the one or more levels of the scope of field of customer support may have one or more of the customer service chatbot 102A from the one or more vendors.

The chatbot switching system 202 categorizes the e-commerce chatbot 102B into the one or more levels of the scope of field of e-commerce. In addition, the one or more levels of the scope of field of e-commerce include but may not be limited to electronics, kitchen, pets, beauty, grocery, sports, fitness, bags, luggage, home décor, and health. Further, the one or more levels of the scope of field of e-commerce include but may not be limited to toys, baby products, car, motorcycle, clothing, footwear, watches, digital cameras, cookware, dining, and daily essentials. However, the one or more levels of the scope of field of e-commerce are not limited to the above-mentioned levels. In an embodiment of the present disclosure, each of the one or more levels of the scope of field of e-commerce may have one or more of the e-commerce chatbot 102B from the one or more vendors.

The chatbot switching system 202 categorizes the food ordering chatbot 102C into the one or more levels of the scope of field of food. In addition, the one or more levels of the scope of field of food include but may not be limited to Italian cuisine, Indian cuisine, Mexican cuisine, Turkish cuisine, Thai cuisine, Greek cuisine, Japanese cuisine, Chinese Cuisine, and Continental cuisine. However, the one or more levels of the scope of field of food are not limited to the above-mentioned levels. In an embodiment of the present disclosure, each of the one or more levels of the scope of field of food may have one or more of the food ordering chatbot 102C from the one or more vendors.

The chatbot switching system 202 categorizes the transactional chatbot 102D into the one or more levels of the scope of field of finance. In addition, the one or more levels of the scope of field of finance include but may not be limited to online payments, car buying loans, house buying loans, credit cards, net banking, commercial banking, opening saving accounts, and home equity. Further, the one or more levels of the scope of field of finance include but may not be limited to stock exchange investment, current account opening, fixed deposits, forex card, health insurance, life insurance, mutual funds, and bill payments. However, the one or more levels of the scope of field of finance are not limited to the above-mentioned levels. In an embodiment of the present disclosure, each of the one or more levels of the scope of field of finance may have one or more of the transactional chatbot 102D from the one or more vendors.

The chatbot switching system 202 categorizes the healthcare chatbot 102E into the one or more levels of the scope of field of health services. In addition, the one or more levels of the scope of field of health services include but may not be limited to ophthalmologists, dermatologists, cardiologists, psychiatrists, gastroenterologists, gynecologists, neurologists, and urologists. Further, the one or more levels of the scope of field of health services include but may not be limited to dentists, prosthodontists, orthodontists, pediatrics, endodontists, homoeopaths, diagnostics and pharmacy. However, the one or more levels of the scope of field of health services are not limited to the above-mentioned levels. In an embodiment of the present disclosure, each of the one or more levels of the scope of field of health services may have one or more of the healthcare chatbot 102E from the one or more vendors.

The chatbot switching system 202 categorizes the education platform 102F into the one or more levels of the scope of field of education. In addition, the one or more levels of the scope of field of education include but may not be limited to Bachelors, Masters, mechanical engineering, computer science, information technology, automobile, electronics, electrical, design, and medical. Further, the one or more levels of the scope of field of education include but may not be limited to fashion design, interior design, graphic design, web design, game design, textile design, visual merchandizing, and law. Furthermore, the one or more levels of the scope of field of education include but may not be limited to hospitality, animation, mass communication, business, management, humanities, social science, architecture, accounts, and commerce. However, the one or more levels of the scope of field of education are not limited to the above-mentioned levels. In an embodiment of the present disclosure, each of the one or more levels of the scope of field of education may have one or more of the education platform 102F from the one or more vendors.

The chatbot switching system 202 categorizes the real estate and housing chatbot 102G into the one or more levels of the scope of field of housing and real estate. In addition, the one or more levels of the scope of field of housing and real estate include but may not be limited to residential real estate, commercial real estate, industrial real estate, apartments, bungalow, cottage, and ranch. Further, the one or more levels of the scope of field of housing and real estate include but may not be limited to townhome, flat, farmhouse, and rented house. However, the one or more levels of the scope of field of housing and real estate are not limited to the above-mentioned levels. In an embodiment of the present disclosure, each of the one or more levels of the scope of field of housing and real estate may have one or more of the real estate and housing chatbot 102G from the one or more vendors.

The chatbot switching system 202 categorizes the travel and tourism chatbot 102H into the one or more levels of the scope of field of travel and tourism. In addition, the one or more levels of the scope of field of travel and tourism include but may not be limited to hotels, apartment stay, resort stay, villa stay, guest houses, hostels, motels, and homestays. Further, the one or more levels of the scope of field of travel and tourism include but may not be limited to flight bookings, train bookings, rental cars, rental bikes, taxi bookings, and bus bookings. However, the one or more levels of the scope of field of travel and tourism are not limited to the above-mentioned levels. In an embodiment of the present disclosure, each of the one or more levels of the scope of field of travel and tourism may have one or more of the travel and tourism chatbot 102H from the one or more vendors.

The one or more vendors are vendors that provide support for the one or more intelligent conversational agents. In general, vendor is a person or company offering something for sale, especially a trader. The one or more intelligent conversational agents are associated with the one or more vendors. In an embodiment of the present disclosure, the one or more vendors are developers the one or more intelligent conversational agents. In another embodiment of the present disclosure, the one or more vendors are owner of the one or more intelligent conversational agents. In yet another embodiment of the present disclosure, the one or more vendors provide support for the one or more intelligent conversational agents.

FIG. 3 illustrates an interactive computing environment 300 for switching and handover between the one or more intelligent conversational agents, in accordance with various embodiments of the present disclosure. The interactive computing environment 300 includes a plurality of users 302, one or more communication devices 304, a communication network 306, and the chatbot switching system 202. In addition, the interactive computing environment 300 includes the online chatbot marketplace 102, a server 308, and a database 310. The components of the interactive computing environment 300 work in conjunction with each other to perform switching and handover between the one or more intelligent conversational agents.

The interactive computing environment 300 includes the plurality of users 302. In an embodiment of the present disclosure, the plurality of users 302 is any person who wants information from a mega bot. In another embodiment of the present disclosure, the plurality of users 302 is any person who wants information for the scope of field from the mega bot. In yet another embodiment of the present disclosure, the plurality of users 302 is any person who wants assistance of various contexts from the mega bot. The mega bot is created by the chatbot switching system 202. In general, chatbot is a piece of software that conducts a conversation via auditory or textual methods. In addition, chatbots are often designed to convincingly simulate how a human would behave as a conversational partner.

The interactive computing environment 300 includes the plurality of users 302. In addition, the plurality of users 302 may be any person or individual accessing the one or more communication devices 304. In an embodiment of the present disclosure, the plurality of users 302 is an owner of the one or more communication devices 304. In another embodiment of the present disclosure, the plurality of users 302 is not the owner of the one or more communication devices 304. In an embodiment of the present disclosure, the plurality of users 302 accesses the one or more communication devices 304 at home. In another embodiment of the present disclosure, the plurality of users 302 accesses the one or more communication devices 304 at a cafe. In yet another embodiment of the present disclosure, the plurality of users 302 accesses the one or more communication devices 304 in an office. In an example, a user U1 accesses a smartphone S1 while sitting in a living room. In another example, a user U2 accesses a laptop L1 while travelling from one place to another. In yet another example, a user U3 accesses a desktop computer D1 while working in the office.

The interactive computing environment 300 includes the plurality of users 302 who is any person present at any location and accessing the mega bot. The plurality of users 302 is any legal person or natural person who initiates conversation with the mega bot and need an IP based network for accessing the mega bot. In addition, the plurality of users 302 is an individual or person who access the online chatbot marketplace 102 and the mega bot on the one or more communication devices 304.

The interactive computing environment 300 includes the one or more communication devices 304 that enable the plurality of users 302 to access the online chatbot marketplace 102 and the mega bot. The one or more communication devices 304 are internet-enabled device to allow the plurality of users 302 to access the online chatbot marketplace 102 and the mega bot. In an embodiment of the present disclosure, each of the one or more communication devices 304 is a portable communication device. The portable communication device includes but may not be limited to a laptop, a smartphone, a tablet, and a smart watch. In an example, the smartphone may be an iOS-based smartphone, an android-based smartphone, a windows-based smartphone and the like. In another embodiment of the present disclosure, each of the one or more communication devices 304 is a fixed communication device. The fixed communication device includes but may not be limited to a desktop, a workstation, a smart TV and a mainframe computer. In an embodiment of the present disclosure, the one or more communication devices 304 are currently in the switched-on state. The one or more communication devices 304 are any type of devices having an active internet. In addition, each of the plurality of users 302 accesses corresponding communication device of the one or more communication devices 304 in real-time.

In an embodiment of the present disclosure, the one or more communication devices 304 perform computing operations based on a suitable operating system installed inside the one or more communication devices 304. In general, the operating system is system software that manages computer hardware and software resources and provides common services for computer programs. In addition, the operating system acts as an interface for software installed inside the one or more communication devices 304 to interact with hardware components of the one or more communication devices 304. In an embodiment of the present disclosure, each of the one or more communication devices 304 perform computing operations based on any suitable operating system designed for the portable communication device. In an example, the operating system installed inside the one or more communication devices 304 is a mobile operating system. Further, the mobile operating system includes but may not be limited to windows operating system, android operating system, iOS operating system, and Sailfish. However, the operating system is not limited to above mentioned operating systems. In an embodiment of the present disclosure, the one or more communication devices 304 operate on any version of particular operating system corresponding to above mentioned operating systems.

In another embodiment of the present disclosure, the one or more communication devices 304 perform computing operations based on any suitable operating system designed for fixed communication device. In an example, the operating system installed inside the one or more communication devices 304 is windows. In another example, the operating system installed inside the one or more communication devices 304 is Mac. In yet another example, the operating system installed inside the one or more communication devices 304 is Linux based operating system. In yet another example, the operating system installed inside the one or more communication devices 304 is Chrome OS. In yet another example, the operating system installed inside the one or more communication devices 304 may be one of UNIX, *Kali* Linux, and the like. However, the operating system is not limited to above mentioned operating systems.

In an embodiment of the present disclosure, the one or more communication devices 304 operate on any version of windows operating system. In another embodiment of the present disclosure, the one or more communication devices 304 operate on any version of Mac operating system. In yet another embodiment of the present disclosure, the one or more communication devices 304 operate on any version of Linux operating system. In yet another embodiment of the present disclosure, the one or more communication devices 304 operate on any version of Chrome OS. In yet another embodiment of the present disclosure, the one or more communication devices 304 operate on any version of particular operating system corresponding to above mentioned operating systems.

The one or more communication devices 304 enable the plurality of users 302 to access the online chatbot marketplace 102 and the mega bot. The one or more communication devices 304 are internet-enabled devices that allow the plurality of users 302 to access one or more applications of the enterprise integrated with the mega bot. In an embodiment of the present disclosure, the one or more applications are installed on the one or more communication devices 304. The one or more applications allow the plurality of users 302 to perform a plurality of activities. In another embodiment of the present disclosure, the one or more applications are run on a plurality of web browsers installed on the one or more communication devices 304. In an example, the plurality of web browsers include but may not be limited to Opera, Mozilla Firefox, Google Chrome, Internet Explorer, Microsoft Edge, Safari and UC Browser. Further, the plurality of web browsers installed on the one or more communication devices 304 runs on any version of the respective web browser of the above mentioned web browsers. In an embodiment of the present disclosure, the plurality of users 302 installs the one or more applications on the one or more communication device 304. In another embodiment of the present disclosure, the plurality of users 302 accesses the one or more applications on the plurality of web browsers installed on the one or more communication devices 304.

In an example, a user U1 connects with the interactive computing environment 300 through a communication device D1 (let's say a smartphone) to access a mega bot M1 (let's say e-commerce related conversation). In another example, a user U2 connects with the computing environment 300 through a communication device D2 (let's say a desktop computer) at home to order food on a mega bot M2. In yet another example, a user U3 connects with the computing environment 300 with a communication device D3 (let's say a tablet) while travelling to make credit card payment on a mega bot M3. In yet another example, a user U4 connects with the computing environment 300 with a communication device D4 (let's say a laptop) at cafe to book appointment with a dentist on a mega bot M4. In yet another example, a user U5 connects with the computing environment 300 with a communication device D5 (let's say a workstation) at home to raise fees query for economics honors on a mega bot M5. In yet another example, a user U6 connects with the computing environment 300 with a communication device D6 (let's say an iPad) at home to search rented apartments on a mega bot M6. In yet another example, a user U7 connects with the computing environment 300 with a communication device D7 (let's say a smartphone) at home to book a hotel room on a mega bot M7.

Each of the one or more communication devices 304 comprises of a memory. In general, the memory includes computer-storage media in the form of volatile and/or non-volatile memory. The memory may be removable, non-removable, or a combination thereof. Exemplary hardware devices include solid-state memory, hard drives, optical-disc drives, etc. The memory is coupled with one or more processors. In general, the one or more processor read data from various entities such as memory or I/O components. The one or more processor execute the one or more instructions which are stored in the memory. The one or more processors provide execution method for one or more instructions provided by the chatbot switching system 202.

The one or more communication devices 304 is a media device. The one or more communication devices 304 enable the plurality of users 302 to perform the plurality of activities on the one or more applications integrated with the mega bot. The one or more communication devices 304 support various multimedia contents. The plurality of users 302 performs the plurality of activities in real-time through the one or more communication devices 304.

The interactive computing environment 300 includes the communication network 306. The one or more communication devices 304 are connected to the communication network 306. The communication network 306 provides a medium for the plurality of users 302 accessing the one or more applications integrated with the mega bot to connect with the chatbot switching system 202. In an embodiment of the present disclosure, the communication network 306 is an internet connection. In another embodiment of the present disclosure, the communication network 306 is a wireless mobile network. In yet another embodiment of the present disclosure, the communication network 306 is a wired network with a finite bandwidth. In yet another embodiment of the present disclosure, the communication network 306 is a combination of the wireless and the wired network for the optimum throughput of data transmission. In yet another embodiment of the present disclosure, the communication network 306 is an optical fiber high bandwidth network that enables a high data rate with negligible connection drops. The communication network 306 includes a set of channels. Each channel of the set of channels supports a finite bandwidth. Moreover, the finite bandwidth of each channel of the set of channels is based on capacity of the communication network 306. The communication network 306 connects the one or more communication devices 304 to the chatbot switching system 202 using a plurality of methods. The plurality of methods used to provide network connectivity to the one or more communication devices 304 includes 2G, 3G, 4G, 5G, Wifi and the like.

The interactive computing environment 300 includes the chatbot switching system 202. The chatbot switching system 202 performs onboarding of the one or more intelligent conversational agents in the online chatbot marketplace 102. The chatbot switching system 202 provides a clean and natural interface for the plurality of users 302 to connect with the mega bot using the one or more communication devices 304. The chatbot switching system 202 creates the mega bot that allows engagements with the plurality of users 302. The plurality of users 302 initiates the conversation and one or more queries with the mega bot. In an embodiment of the present disclosure, the plurality of users 302 is involved in the conversation with the mega bot. The mega bot provides responses to the plurality of users 302. The mega bot responds to the one or more queries of the plurality of users 302 based on selection and switching of the one or more intelligent conversational agents.

The chatbot switching system 202 creates the online chatbot marketplace 102 to enable the one or more vendors to upload the one or more intelligent conversational agents. In addition, the online chatbot marketplace 102 enables the enterprise to access the one or more intelligent conversational agents from the one or more vendors. Further, each of the one or more intelligent conversational agents is affiliated with the scope of field. Furthermore, the chatbot switching system 202 categorizes each of the one or more intelligent conversational agents into the one or more levels of the plurality of categories. Moreover, the plurality of categories include but may not be limited to trusted conversational agents, untrusted conversational agents, and the scope of field. Also, the scope of field include but may not be limited to customer support, e-commerce, food, housing and real estate, finance, travel and tourism, health services, and education.

The chatbot switching system 202 integrates the one or more intelligent conversational agents to create the mega bot in real-time. In addition, each of the one or more intelligent conversational agents has a trust score. Further, the trust score is dependent on a plurality of factors associated with the one or more intelligent conversational agents. Furthermore, the chatbot integration system generates the mega bot based on the integration of the one or more intelligent conversational agents having the trust score. Moreover, the chatbot switching system 202 computes the trust score for each of the one or more intelligent conversational agents uploaded on the online chatbot marketplace 102 by the one or more vendors. Also, the chatbot switching system 202 ranks each of the one or more intelligent conversational agents in the online chatbot marketplace 102 based on the trust score.

The chatbot switching system 202 receives a first set of data in real-time. In addition, the first set of data is associated with the plurality of users 302. Further, the first set of data include but may not be limited to user behavioral information, past engagements with conversational agents and user profile information. Furthermore, the chatbot switching system 202 collects a second set of data in real-time. Moreover, the second set of data is associated with the one or more intelligent conversational agents. Also, the second set of data includes the trust score associated with each of the one or more intelligent conversational agents, and confidence level of the one or more intelligent conversational agents. Also, the second set of data includes past performance of the one or more intelligent conversational agents, performance of each of the one or more intelligent conversational agents in a virtual environment, and the like.

The chatbot switching system 202 fetches the one or more queries from the plurality of users 302 for the mega bot. In addition, the one or more queries are associated to the scope of field. Further, each of the one or more queries has a plurality of aspects. Furthermore, the plurality of aspects include but may not be limited to context, linguistic style, sentence construction, and lexical ambiguity. Moreover, the chatbot switching system 202 receives confidence level of the one or more intelligent conversational agents for responding to the one or more queries of the plurality of users 302. Also, each of the one or more intelligent conversational agents claims to have the confidence level to create responses for the one or more queries. Also, the chatbot switching system 202 normalizes the trust score of each of the one or more intelligent conversational agents based on each of the plurality of factors.

The chatbot switching system 202 analyzes the first set of data, the second set of data and the one or more queries using one or more machine learning algorithms in real-time. The analysis is performed based on training of a machine learning model. The analysis is performed to enable selection of a suitable intelligent conversational agent from the one or more intelligent conversational agents. In an embodiment of the present disclosure, the one or more machine learning algorithms include a decision tree algorithm and a random forest algorithm. In another embodiment of the present disclosure, the one or more machine learning algorithms include but may not be limited to prediction algorithms, deep learning algorithms, natural language processing algorithm and the like. However, the one or more machine learning algorithms are not limited to the above-mentioned algorithms.

In addition, the chatbot switching system 202 creates the machine learning model to perform analysis of the first set of data, the second set of data, and the one or more queries. The machine learning model is trained to identify patterns of journey and the plurality of aspects. The machine learning model is trained to analyze the first set of data, the second set of data, and the one or more queries. In an embodiment of the present disclosure, the machine learning model is trained using supervised machine learning model. In another embodiment of the present disclosure, the machine learning model is trained using un-supervised machine learning model. In addition, the machine learning model predicts behavior of each of the plurality of users 302 based on the first set of data and the plurality of aspects of the one or more queries. Further, the behavior of the plurality of users 302 is predicted in real-time.

The chatbot switching system 202 selects the suitable intelligent conversational agent from the one or more intelligent conversational agents having the trust score above a threshold level according to the plurality of aspects of each of the one or more queries. The selection is based on the plurality of factors and analysis of the first set of data, the second set of data and the one or more queries. In addition, the mega bot selects the suitable intelligent conversational agent from the one or more intelligent conversational agents. Further, the threshold level is defined by the enterprise. Furthermore, the plurality of factors include but may not be limited to identification of the plurality of aspects, the confidence level of the one or more intelligent conversational agents, and past performance of the one or more intelligent conversational agents. Moreover, the plurality of factors include but may not be limited to behavior identification of the plurality of users 302, automated testing performance of the one or more intelligent conversational agents and cost of engagement with the one or more intelligent conversational agents. Also, the plurality of factors include but may not be limited to performance of each of the one or more intelligent conversational agents in a virtual environment, and a feedback from the plurality of users 302.

The chatbot switching system 202 creates the responses for the one or more queries at the mega bot using the suitable intelligent conversational agent from the one or more intelligent conversational agents. In addition, the responses are sent to the plurality of users 302 on the one or more communication devices 304. Further, the chatbot switching system 202 enables the one or more intelligent conversational agents to create a secondary response for the one or more queries in the virtual environment with a privacy rule limitation. The privacy rule limitation corresponds to sharing the one or more queries with the one or more intelligent conversational agents not the first set of data with the one or more intelligent conversational agents. The privacy rule limitation limits sharing of user profile information with the one or more intelligent conversational agents. Furthermore, the secondary response enables the chatbot switching system 202 to monitor performance of the one or more intelligent conversational agents in the virtual environment in real-time. Moreover, the virtual environment is provided to the one or more intelligent conversational agents to create the secondary response for the one or more queries to improve ranking of the one or more intelligent conversational agents. Also, the chatbot switching system 202 analyzes the second response of the one or more intelligent conversational agents to improve ranking and the trust score of the one or more intelligent conversational agents.

The chatbot switching system 202 switches between the one or more intelligent conversational agents in the mega bot interacting with the plurality of users based on the plurality of aspects of corresponding query of the one or more queries and the plurality of factors. The chatbot switching system 202 predicts the journey of the conversation between the plurality of users and the mega bot based on analysis performed on the first set of data, the second set of data, and the one or more queries. In addition, the chatbot switching system 202 predicts the journey of the conversation between the plurality of users and the mega bot using the one or more machine learning algorithms. Further, the chatbot switching system 202 detects the plurality of aspects associated with the one or more queries using the machine learning model in real-time. Furthermore, the chatbot switching system 202 determines transition of the plurality of aspects within the conversation between the plurality of users and the mega bot based on analysis performed on the one or more queries. Moreover, the chatbot switching system 202 determines the transition of the plurality of aspects within the conversation between the plurality of users and the mega bot using the one or more machine learning algorithms. The determination of the transition of the plurality of aspects within the conversation enables the chatbot switching system 202 to switch between the one or more intelligent conversational agents in the mega bot interacting with the plurality of users.

The chatbot switching system 202 obtains the feedback from each of the plurality of users 302 on the responses and the secondary response of each of the one or more intelligent conversational agents for the one or more queries. In addition, the chatbot switching system 202 tests each of the one or more intelligent conversational agents with an automated testing query in real-time. Further, the testing determines the automated testing performance of each of the one or more intelligent conversational agents that enables the chatbot switching system 202 to compute the trust score.

The mega bot communicates with the plurality of users 302 on the scope of field. The chatbot switching system 202 enables integration of the one or more intelligent conversational agents from the one or more vendors. The one or more vendors are vendors that provide support for the one or more intelligent conversational agents. In general, vendor is a person or company offering something for sale, especially a trader. The one or more intelligent conversational agents are associated with the one or more vendors. In an embodiment of the present disclosure, the one or more vendors are developers of the one or more intelligent conversational agents. In another embodiment of the present disclosure, the one or more vendors are owner of the one or more intelligent conversational agents. In yet another embodiment of the present disclosure, the one or more vendors provide support for the one or more intelligent conversational agents.

The chatbot switching system 202 receives information associated with context, theme, and subject matter of the conversation and the one or more queries to switch between the one or more intelligent conversational agents. The chatbot switching system 202 recognizes authenticity of the one or more intelligent conversational agents in real-time. The chatbot switching system 202 recognizes the one or more intelligent conversational agents with malicious goals or intentions. The chatbot switching system 202 computes the trust score to recognize the one or more intelligent conversational agents with malicious goals or intentions. The chatbot switching system 202 computes the trust score during onboarding of the one or more intelligent conversational agents. The chatbot switching system 202 computes the trust score for each new conversational agent of the one or more intelligent conversational agents. In an embodiment of the present disclosure, the chatbot switching system 202 is associated with the enterprise. In general, enterprise is considered as large corporation that manage hundreds or even thousands of employees. In an embodiment of the present disclosure, the enterprise owns the chatbot switching system 202. In another embodiment of the present disclosure, the chatbot switching system 202 allows the enterprise to determine level of trust in the trust score of the one or more intelligent conversational agents.

In an embodiment of the present disclosure, the chatbot switching system 202 determines the trust score initially by vendor reputation. In general, vendor reputation is the most important factor to determine the likelihood of long-term satisfaction with a vendor and their products. Further, the chatbot switching system 202 determines the trust score through running the automated testing for the one or more intelligent conversational agents. The automated testing determines performance of the one or more intelligent conversational agents with different inputs and contexts within a sandbox environment. The performance of the one or more intelligent conversational agents facilitates to detect the one or more intelligent conversational agents with unexpected results.

In an embodiment of the present disclosure, the mega bot is connected with various APIs to connect to one or more payment partners. In an example, user A is chatting with the mega bot to get recommendations for an insurance for his motor vehicle. The mega bot provides various available insurance options. In addition, the user A selects one of the available insurance options. Further, the mega bot connects the user A with the one or more payment partners (or online digital wallet providers) and provides various payment options (such as netbanking, upi payment, paytm, google pay, phonepe, bhim and the like) to the user A to complete the payment securely without leaving the mega bot.

In an embodiment of the present disclosure, the chatbot switching system 202 fetches various device parameters of the one or more communication devices 304 of the plurality of users 302. In an example, the device parameters include GPS permission, camera access, gyroscope information, data from various sensors of the device, and the like. The chatbot switching system 202 utilizes the device parameters to provide additional functionality to the mega bot. In an example, the mega bot tracks the device information of the one or more communication devices 304 of the plurality of users 302 in real-time. In an example, a user U1 accesses a mega bot M1 to take consultation from the mega bot M1 for various mutual funds available based on risk profile of the user U1. In addition, the mega bot M1 provides response to the user U1. Further, the user U1 may prefer to go and get a mutual fund policy offline by personally visiting branch office. Furthermore, the mega bot M1 provides recommendations of the nearby available banks or enterprises that can provide the mutual fund facility to the user U1 based on the location data of a communication device D1 (let's say a smartphone) of the user U1.

In an embodiment of the present disclosure, the mega bot accesses camera of the one or more communication devices 304 of the plurality of users 302 to capture real-time image of the plurality of user 302. In addition, the mega bot captures the real-time image of the plurality of users 302 for performing facial identification of the plurality of users 302 to provide enhanced security to the plurality of users 302 in real-time. In another embodiment of the present disclosure, the mega bot accesses fingerprint scanner of the one or more communication devices 304 of the plurality of users 302 to take real-time fingerprint information of the plurality of users 302. Further, the mega bot takes the fingerprints of the plurality of users 302 in real-time for performing biometric authentication of the plurality of users 302 to provide enhanced security.

In an embodiment of the present disclosure, the chatbot switching system 202 performs switching between the one or more intelligent conversational agents based on the trust score of the one or more intelligent conversational agents. In another embodiment of the present disclosure, the chatbot switching system 202 performs switching between the one or more intelligent conversational agents based on past performance of the one or more intelligent conversational agents. In yet another embodiment of the present disclosure, the chatbot switching system 202 performs switching between the one or more intelligent conversational agents based on cost of engagement of the one or more intelligent conversational agents. In yet another embodiment of the present disclosure, the chatbot switching system 202 performs switching between the one or more intelligent conversational agents based on the feedback of the plurality of users 302. In yet another embodiment of the present disclosure, the chatbot switching system 202 performs switching between the one or more intelligent conversational agents based on the scope of field of the conversation and the one or more queries.

In an embodiment of the present disclosure, each of the one or more intelligent conversational agents is incentivized to proactively switch to a better agent of the one or more intelligent conversational agents. The chatbot switching system 202 encourages switching and handover between the one or more intelligent conversational agents. In an embodiment of the present disclosure, the chatbot switching system 202 performs the switching between the one or more intelligent conversational agents based on the behavior and the journey of the plurality of users 302. In an embodiment of the present disclosure, the behavior of the plurality of users 302 is determined by sentiment analysis and analysis of context of the one or more queries of the plurality of users 302. In an embodiment of the present disclosure, the chatbot switching system 202 provides a switching probability score to the one or more intelligent conversational agents. In addition, agent from the one or more intelligent conversational agents having highest switching probability score becomes next suitable intelligent conversational agent after performing switch from the current agent. In an embodiment of the present disclosure, the chatbot switching system 202 preloads the next suitable intelligent conversational agent of the one or more intelligent conversational agents. The preloading of the next suitable intelligent conversational agent is done in order to provide seamless experience to the plurality of users 302. In addition, the preloading of the next suitable intelligent conversational agent reduces latency for the plurality of users 302.

In an embodiment of the present disclosure, the next suitable intelligent conversational agent has confidence score higher than confidence score of the current agent in order to perform switching. In addition, the switching between the one or more intelligent conversational agents corresponds to switching of data between the one or more intelligent conversational agents. Further, the chatbot switching system 202 enables switching of data between the one or more intelligent conversational agents taking care of security and privacy of data. In an embodiment of the present disclosure, the one or more intelligent conversational agents are connected to a plugin or API. The plugin analyzes the behavior of the plurality of users 302 and context of conversations or engagements in real-time. In addition, the plugin determines the confidence level or score that determines likeliness of switch between the one or more intelligent conversational agents.

In an embodiment of the present disclosure, the plugin preloads the next suitable intelligent conversational agent for switching with the current agent of the suitable intelligent conversational agent in the mega bot. In addition, the next suitable intelligent conversational agent is allowed to access the conversation between the plurality of users 302 and the current agent within the mega bot.

In an embodiment of the present disclosure, the chatbot switching system 202 uses historical conversations or interactions across the one or more intelligent conversational agents and used cases to determine context of the conversation or engagement with the plurality of users 302. In addition, the chatbot switching system 202 uses historical conversations/interactions across the one or more intelligent conversational agents and used cases to determine change in context of the conversation with the plurality of users 302. In an example, the chatbot switching system 202 determines change in context from FAQ chatbot to insurance comparison chatbot to insurance purchase chatbot.

In an example, a user U1 raises a query Q1 (let's say query related to bachelor of technology) to a mega bot M1. In addition, the mega bot M1 selects a suitable chatbot C1 (Let's say educational chatbot efficient in responding to queries related to bachelor of technology) to respond to the query Q1 based on context of the query Q1 and trust score of the suitable chatbot C1. Further, the suitable chatbot C1 responds with a response R1 relevant to conversation and the query Q1. Furthermore, the mega bot M1 allows other chatbots (Let's say other educational chatbots) to prepare a secondary response S1 for the query Q1 in a virtual environment V1. Moreover, the user U1 raises a query Q2 (let's say query related to Master of Engineering) in the continuation to the response R1 in same conversation. Also, the mega bot M1 switches to a suitable chatbot C2 (Let's say educational chatbot efficient in responding to queries related to Master of Engineering) from the suitable chatbot C1 based on context of the query Q2 and trust score of the suitable chatbot C2. Also, the mega bot may continuously switch between various chatbots based on the context of the conversation and query. Also, the mega bot M1 asks for feedback from the user U1 for the conversation.

In another example, a user U2 raises a query Q3 (let's say query related to material science courses) to a mega bot M2. In addition, the mega bot M2 selects a suitable chatbot C3 (Let's say educational chatbot efficient in responding to queries related to material science courses) to respond to the query Q3 based on context of the query Q3 and trust score of the suitable chatbot C3. Further, the suitable chatbot C3 responds with a response R2 relevant to conversation and the query Q3. Furthermore, the mega bot M2 allows other chatbots (Let's say other educational chatbots) to prepare a secondary response S2 for the query Q3 in a virtual environment V2. Moreover, the user U2 raises a query Q4 (let's say query related to machine learning and artificial intelligence courses) in the continuation to the response R2 in same conversation. Also, the mega bot M2 switches to a suitable chatbot C4 (Let's say educational chatbot efficient in responding to queries related to machine learning and artificial intelligence courses) from the suitable chatbot C3 based on context of the query Q4 and trust score of the suitable chatbot C4. Also, the mega bot may continuously switch between various chatbots based on the context of the conversation and query. Also, the mega bot M2 asks for feedback from the user U2 for the conversation.

In yet another example, a user U3 raises a query Q5 (let's say query related to online shopping of trimmers) to a mega bot M3. In addition, the mega bot M3 selects a suitable chatbot C5 (Let's say e-commerce chatbot efficient in responding to queries related to trimmers) to respond to the query Q5 based on context of the query Q5 and trust score of the suitable chatbot C5. Further, the suitable chatbot C5 responds with a response R3 relevant to conversation and the query Q5. Furthermore, the mega bot M3 allows other chatbots (Let's say other e-commerce chatbots) to prepare a secondary response S3 for the query Q5 in a virtual environment V3. Moreover, the user U3 raises a query Q6 (let's say query related to online shopping of cosmetic products) in the continuation to the response R3 in same conversation. Also, the mega bot M3 switches to a suitable chatbot C6 (Let's say e-commerce chatbot efficient in responding to queries related to cosmetic products) from the suitable chatbot C5 based on context of the query Q6 and trust score of the suitable chatbot C6. Also, the mega bot M3 may continuously switch between various chatbots based on the context of the conversation and query. Also, the mega bot M3 asks for feedback from the user U3 for the conversation.

In yet another example, a user U4 raises a query Q7 (let's say query related to flights tickets) to a mega bot M4. In addition, the mega bot M4 selects a suitable chatbot C7 (Let's say travel and tourism chatbot efficient in responding to queries related to flights tickets) to respond to the query Q7 based on context of the query Q7 and trust score of the suitable chatbot C7. Further, the suitable chatbot C7 responds with a response R4 relevant to conversation and the query Q7. Furthermore, the mega bot M4 allows other chatbots (Let's say other travel and tourism chatbots) to prepare a secondary response S4 for the query Q7 in a virtual environment V4. Moreover, the user U4 raises a query Q8 (let's say query related to train tickets) in the continuation to the response R4 in same conversation. Also, the mega bot M4 switches to a suitable chatbot C8 (Let's say travel and tourism chatbot efficient in responding to queries related to train tickets) from the suitable chatbot C7 based on context of the query Q8 and trust score of the suitable chatbot C8. Also, the mega bot M4 may continuously switch between various chatbots based on the context of the conversation and query. Also, the mega bot M4 asks for feedback from the user U4 for the conversation.

The interactive computing environment 300 includes the server 308 and the database 310. The chatbot switching system 202 is associated with the server 308. In general, server is a computer program or device that provides functionality for other programs or devices. The server 308 provides various functionalities, such as sharing data or resources among multiple enterprises, or performing computation for the enterprise. However, those skilled in the art would appreciate that the chatbot switching system 202 is connected to more number of servers. Furthermore, it may be noted that the server 308 includes the database 310. However, those skilled in the art would appreciate that more number of the servers include more numbers of database.

In an embodiment of the present disclosure, the chatbot switching system 202 is located in the server 308. In another embodiment of the present disclosure, the chatbot switching system 202 is connected with the server 308. In yet another embodiment of the present disclosure, the chatbot switching system 202 is a part of the server 308. The server 308 handles each operation and task performed by the chatbot switching system 202. The server 308 stores one or more instructions for performing the various operations of the chatbot switching system 202. The server 308 is located remotely from the chatbot switching system 202. The server 308 is associated with an administrator. In general, administrator manages the different components in the chatbot switching system 202. The administrator coordinates the activities of the components involved in the chatbot switching system 202. The administrator is any person or individual who monitors the working of the chatbot switching system 202 and the server 308 in real-time. The administrator monitors the working of the chatbot switching system 202 and the server 308 through a communication device. The communication device includes the laptop, the desktop computer, the tablet, a personal digital assistant and the like.

The database 310 stores different sets of information associated with various components of the chatbot switching system 202. In general, database is used to hold general information and specialized data, such as characteristics data of the plurality of users 302, data of the one or more communication devices 304, data of the one or more online applications and the like. The database 310 stores the information of the one or more applications, the first set of data, the profiles of the plurality of users 302, demographic information of the plurality of users 302 and the like. The database 310 organizes the data using model such as relational models or hierarchical models. Further, the database 310 stores data provided by the administrator.

FIG. 4 illustrates a general overview of the chatbot switching system 202, in accordance with various embodiments of the present disclosure. The chatbot switching system 202 includes a mega-agent controller module, specialized agents module, a user/DMP module, a recommendation module, and an engagement module. The mega-agent controller module includes a smart router, a profile engine, normalization, an engagement engine, a consolidator, an agent selector, and the online chatbot marketplace 102. The specialized agents module includes a survey, a poll, book a service, an e-commerce, an events and FAQs. The user/DMP module includes an authentication, a profile, roles, behavioral, and DMP. The recommendation module includes most popular, role based, interest based, behavioural based, profile based, and AI/ML based. The engagement module includes look-alike, multi-channel push, channel repurposing, segment builder, events, and channel selector.

The mega-agent controller module provides input to the chatbot switching system 202. The mega-agent controller module handles engagement of the plurality of users 302 and various coordinates between different components of the chatbot switching system 202. The mega-agent controller module interfaces with one or more channels. The one or more channels include email, messaging system, chatbots, voice engagements and the like. Further, the mega-agent controller module coordinates with internal system before responding back to the plurality of users 302. The term internal system represents components of the mega-agent controller module. The smart router handles communication from the plurality of users 302 and selects any of the one or more intelligent conversational agents to run internally. The smart router selects any of the one or more intelligent conversational agents based on a plurality of factors. The plurality of factors includes previous engagements, current question, state of the plurality of users 302, profile of the plurality of users 302, the recommendation module, and the one or more intelligent conversational agents.

In an embodiment of the present disclosure, each of the one or more intelligent conversational agents has pipeline structure. In another embodiment of the present disclosure, each of the one or more intelligent conversational agents has tree structure. In yet another embodiment of the present disclosure, each of the one or more intelligent conversational agents has graph structure. In yet another embodiment of the present disclosure, each of the one or more intelligent conversational agents has any suitable structure of the like.

The chatbot switching system 202 calls each of the one or more intelligent conversational agents by a predetermined flow or route for the pipeline structure. In an example, the predetermined flow or route is "Pull out profile information about the plurality of users 302, Pull out historical transactions, call chatbot A, call chatbot B". The smart router makes call to the chatbot switching system 202. In addition, one or more information is passed to the chatbot switching system 202 during each call of the smart router made to the system. The one or more information includes a profile of the plurality of users 302, and details of the plurality of users 302. In addition, the one or more information includes control information that may be passed from a previous agent of the one or more intelligent conversational agents to a future agent of the one or more intelligent conversational agents. Further, the one or more information includes tag cloud of the plurality of users 302. The tag cloud of the plurality of users 302 includes a summary of the plurality of users 302 for the one or more intelligent conversational agents.

In an embodiment of the present disclosure, the one or more intelligent conversational agents are implemented using a tree structure. In a tree structure, the multiple requests are optimized at the same time instead of waiting for each of the one or more intelligent conversational agents to respond instead of calling each of the one or more intelligent conversational agents sequentially. In another embodiment of the present disclosure, the one or more intelligent conversational agents are implemented using graph structure. In general, a parent exists upon various components of system in a graph structure. The graph structure allows information or data to share easily from the agent of the one or more intelligent conversational agents to other agent of the one or more intelligent conversational agents and vice versa. In an example, the information is easily shared from agent A to agent B and vice versa using the tree structure.

The profile engine accumulates information about the plurality of users 302 through one or more channels. The profile engine associates information about the plurality of users 302 with the tag cloud of the plurality of users 302. In addition, the plurality of users 302 is able to see interests of the plurality of users 302 based on factors such as what the plurality of users 302 has typed, spoken, browsed, clicked on, engaged with and the like. In addition, each factor has different weightage associated with the factor. Further, the profile engine determines satisfaction of the plurality of users 302 from the engagement with the chatbot. The profile engine determines satisfaction of the plurality of users 302 based on responses back from the plurality of users 302 and subsequent responses. Furthermore, the profile engine determines satisfaction of the plurality of users 302 based on sentiment analysis of subsequent response. In an embodiment of the present disclosure, the profile engine determines satisfaction of the plurality of users 302 based on behavioral analysis of the plurality of users 302. In an example, the chatbot switching system 202 asks same engagement and utilizes same responses in the past to determine general satisfaction for question. In another embodiment of the present disclosure, the profile engine determines satisfaction of the plurality of users 302 based on subsequent delays in response from the plurality of users 302. In an example, frequent stops, bounces from one question to another question, asking to speak to a human agent and the like represents that the plurality of users 302 is frustrated. Also, the profile engine counts the tags weighted by the type of engagement. In an example, type of engagement includes viewing a response, clicking, swiping to read more information and the like.

The profile engine has a mechanism to age data or information of the plurality of users 302 to capture change in behavior of the plurality of users 302 over time. The profile engine captures the change by windowing certain time ranges of data. In addition, the profile engine removes the data or information after a specific age. The profile engine determines confidence of the profile. The confidence of the profile is a function of weightage and age of the information.

The mega-agent controller module performs the normalization. The normalization ensures removal of irregularities in the trust score for each of the one or more intelligent conversational agents to accurately select the suitable intelligent conversational agent from the one or more intelligent conversational agents. The normalization ensures that the data of the plurality of users 302 does not become noisy. In an example, an agent A1 claims 90 percent confidence level in resolving a query Q1 of a user U1. In addition, an agent A2 claims 80 percent confidence level in resolving the query Q1 of the user U1. Further, the chatbot switching system 202 detects that accuracy of resolving the query Q1 by the agent A1 is lower than what is claimed. Furthermore, the chatbot switching system 202 normalizes the trust score of the agent A1. Moreover, the chatbot switching system 202 detects that accuracy of resolving the query Q1 by the agent A2 is higher than what is claimed. Furthermore, the chatbot switching system 202 normalizes the trust score of the agent A2.

The normalization facilitates in removal of bad actors. The bad agent of the one or more intelligent conversational agents may corrupt the trust score. The chatbot switching system 202 performs normalization to give bad tags to the bad agents of the one or more intelligent conversational agents. The chatbot switching system 202 tracks bad tags within the chatbot switching system 202. The chatbot switching system 202 tracks bad tags only after identification of concrete data. The chatbot switching system 202 identifies inaccuracy of the recommendation and removes the tags. The chatbot switching system 202 performs correlation to identify the one or more intelligent conversational agents that provides false indication and claims. Further, the chatbot switching system 202 tweaks the weightage of the one or more intelligent conversational agents or removes ability of the one or more intelligent conversational agents to provide profile for the specific tag.

The engagement engine tracks engagement of the plurality of users 302 for future engagements. In addition, the engagement engine provides notifications to the plurality of users 302 while the plurality of users 302 engages with the chatbot switching system 202. The engagement engine tracks engagements for a specific time interval (say 30 minutes or 1 hour). Further, the engagement engine tracks engagements by interest of the plurality of users 302, sentiment analysis, type of engagement, and the like. In an embodiment of the present disclosure, the tracked engagements are used to determine whether the chatbot switching system 202 must send notifications via email, text message, flash message, via chatbot, mobile engagements and the like.

The engagement engine sends out useful and important notifications to the plurality of users 302. In an embodiment of the present disclosure, the engagement engine sends time sensitive notifications to the plurality of users 302. In an example, the engagement engine only sends notification for a sale ending soon rather than spamming the plurality of users 302 with notifications of products if the plurality of users 302 is involved in conversation with the e-commerce chatbot 102B of the one or more intelligent conversational agents for shopping purpose. In another embodiment of the present disclosure, the engagement engine sends topic sensitive notifications to the plurality of users 302. In an example, the engagement engine notifies the plurality of users 302 that points are awarded if the plurality of users 302 engages in x number of interactions with the one or more intelligent conversational agents.

In yet another embodiment of the present disclosure, the engagement engine sends out location sensitive notifications to the plurality of users 302. In an example, the engagement engine sends location sensitive notifications to the plurality of users 302 if the plurality of users 302 is in an area close to a notification serviceable area. The engagement engine sends the location sensitive notifications while the plurality of users 302 is engaging with the chatbot switching system 202. The engagement engine sends notifications to the plurality of users 302 in real-time when the plurality of users 302 is engaged with the chatbot switching system 202.

The chatbot switching system 202 switches between the one or more intelligent conversational agents. In addition, the chatbot switching system 202 calls the one or more intelligent conversational agents and receives responses from the one or more intelligent conversational agents. The chatbot switching system 202 calls the one or more intelligent conversational agents to enhance profile data by the questions being asked, enhance profile by the responses given, sentiment analysis, the confidence level and the like. The consolidator consolidates responses from the one or more intelligent conversational agents and stores the information. The recommendation engine consolidates responses from the one or more intelligent conversational agents to offer suggestions to the plurality of users 302.

The one or more intelligent conversational agents interact with the chatbot switching system 202 in real-time. The agent selector determines response with highest priority to the plurality of users 302. In an embodiment of the present disclosure, the agent selector determines response based on confidence of answering the question by agent of the one or more intelligent conversational agents. In another embodiment of the present disclosure, the agent selector determines response based on reduction of chance of switching between the one or more intelligent conversational agents if the previous response is provided by the same chatbot. In an example, if same confidence is provided by two agents, the priority must be given to current agent rather than switching of the one or more intelligent conversational agents. In yet another embodiment of the present disclosure, the agent selector determines response based on confidence between the one or more intelligent conversational agents provided by the recommendation engine. In yet another embodiment of the present disclosure, the agent selector determines responses based on a combination of the above mentioned factors. In an embodiment of the present disclosure, the agent selector handles the bad agents. The agent selector determines whether confidence level must be adjusted for response of the agent if dissatisfaction to the answer is known.

The online chatbot marketplace 102 allows the one or more intelligent conversational agents from the one or more vendors, cloud, NLPs, chats, channels, and the like. The online chatbot marketplace 102 includes components such as onboarding, ranking, security, SaaS vs local deployments, trial, testing, and the like. The online chatbot marketplace 102 allows sharing of data or information across the one or more vendors. The online chatbot marketplace 102 includes information that may be sensitive to the enterprise in terms of their processes, systems in place, personal information of the plurality of users 302 and the like. The online chatbot marketplace 102 secures information that is shared between the one or more intelligent conversational agents.

The chatbot switching system 202 onboards the one or more intelligent conversational agents in the online chatbot marketplace 102. The chatbot switching system 202 categorizes the one or more intelligent conversational agents as untrusted and trusted. In an embodiment of the present disclosure, few agents of the one or more intelligent conversational agents include warnings that data sent to the few agents of the one or more intelligent conversational agents may be transferred to the server 308. In an embodiment of the present disclosure, the chatbot switching system 202 categorizes the one or more intelligent conversational agents as untrusted if the one or more intelligent conversational agents includes the above mentioned warnings. In an embodiment of the present disclosure, the chatbot switching system 202 provides option to owner of the chatbot switching system 202 to sandbox the one or more intelligent conversational agents. The chatbot switching system 202 performs sandbox of the one or more intelligent conversational agents by not sending any sensitive information of the plurality of users 302 to the one or more intelligent conversational agents. In addition, the chatbot switching system 202 performs sandbox of the one or more intelligent conversational agents by placing the sandbox around the one or more intelligent conversational agents to ensure no external access or only allow access to the one or more intelligent conversational agents whitelisted by the chatbot switching system 202. In another embodiment of the present disclosure, the chatbot switching system 202 categorizes the one or more intelligent conversational agents as trusted only if the one or more intelligent conversational agents go through the certification process. The certification process facilitates to classify what type of information is getting generated or used by the chatbot switching system 202.

In an embodiment of the present disclosure, the chatbot switching system 202 handles data privacy of the plurality of users 302 while onboarding of the one or more intelligent conversational agents. The data privacy of the plurality of users 302 is essential because the one or more intelligent conversational agents have direct access to information of the plurality of users 302. There is a likelihood that the one or more intelligent conversational agents have access to confidential information (such as ID documents, credit card details) of the plurality of users 302. Therefore, the chatbot switching system 202 identifies and handles the data privacy of the plurality of users 302.

The chatbot switching system 202 performs ranking of the one or more intelligent conversational agents. In an embodiment of the present disclosure, the chatbot switching system 202 performs ranking to determine the one or more intelligent conversational agents. The chatbot switching system 202 performs ranking based on one or more attributes. In an embodiment of the present disclosure, an attribute of the one or more attributes include amount of data and information passed to the one or more intelligent conversational agents. In another embodiment of the present disclosure, another attribute of the one or more attributes include intelligence passed to the one or more intelligent conversational agents. In an example, the one or more intelligent conversational agents may not be able to engage with the plurality of users 302 if the one or more intelligent conversational agents are uninformed about demographic information (say country, age, sex and the like) of the plurality of users 302. In yet another embodiment of the present disclosure, another attribute of the one or more attributes include time period since the one or more intelligent conversational agents are running and engaged with the plurality of users 302. In yet another embodiment of the present disclosure, all above mentioned attributes of the one or more attributes impact capability of the one or more intelligent conversational agents.

In an embodiment of the present disclosure, the chatbot switching system 202 performs the ranking based upon the A/B/n testing. In general, A/B/n testing is a type of testing where each agent of the one or more intelligent conversational agents is compared against each other to determine which has the highest conversion rate. In an embodiment of the present disclosure, the A/B/n testing is performed to identify satisfaction of population in aggregate. In another embodiment of the present disclosure, the A/B/n testing is performed to identify sentiment analysis of users (over time and engagement). In yet another embodiment of the present disclosure, the A/B/n testing is performed to identify amount of dead ends encountered by the plurality of users 302 in each agent of the one or more intelligent conversational agents. In yet another embodiment of the present disclosure, the A/B/n testing is performed to identify generic breakdown of tests, engagements, and the like.

The A/B/n testing is used to fairly determine the agent of the one or more intelligent conversational agents. In addition, the A/B/n testing is used to determine the ranking of the one or more intelligent conversational agents by category based on live tests. In addition, generic information running stats of the chatbot switching system 202 may be sent to the online chatbot marketplace 102 to help rank usage in the chatbot switching system 202.

The chatbot switching system 202 is responsible for security of the one or more intelligent conversational agents. The chatbot switching system 202 is responsible for prevention of data loss, data sovereignty, data compliance, security of the one or more intelligent conversational agents, security of information of the plurality of users 302, and the like. The chatbot switching system 202 checks incoming and outgoing information between the one or more intelligent conversational agents for prevention of data loss of the plurality of users 302. In an embodiment of the present disclosure, the chatbot switching system 202 determines incoming information with some probability. In an example, the chatbot switching system 202 determines sensitive information (such as IDs, credit card information and the like) and tracks the one or more intelligent conversational agents that have access to such type of information.

The chatbot switching system 202 is responsible for security of outgoing information (information passed by and within the one or more intelligent conversational agents and information passed to the plurality of users 302). The chatbot switching system 202 manages data sovereignty through third-party services tied down to a particular country or a solution deployed locally. The communication from the one or more intelligent conversational agents must be described transparently to allow owner of the one or more intelligent conversational agents to inspect or determine information requested by the mega bot of the chatbot switching system 202. The marketplace categorizes data compliance of each of the one or more intelligent conversational agents along with keeping security precautions in place. The chatbot switching system 202 provides security to the one or more intelligent conversational agents by enabling a firewall before and/or after the one or more intelligent conversational agents. In addition, the chatbot switching system 202 may have specific rules to remove any specific information before or after the one or more intelligent conversational agents are called. The chatbot switching system 202 secures sensitive information of the plurality of users 302. The chatbot switching system 202 asks the one or more intelligent conversational agents to declare how the chatbot switching system 202 handles, processes and stores sensitive information of the plurality of users 302.

In an embodiment of the present disclosure, the chatbot switching system 202 supports SaaS (cloud based deployments). In another embodiment of the present disclosure, the chatbot switching system 202 supports cloud private cloud deployments. In yet another embodiment of the present disclosure, the chatbot switching system 202 supports local deployments. In an example, the chatbot switching system 202 supports local deployment of the megabit if owner of the one or more intelligent conversational agents are concerned about the location of servers, processing and data storage.

In an embodiment of the present disclosure, the online chatbot marketplace 102 is an important component of the chatbot switching system 202. In an embodiment of the present disclosure, the administrator of the mega-agent controller has ability to see rank and performance of the one or more intelligent conversational agents. In another embodiment of the present disclosure, the administrator of the mega-agent controller has anonymized statistics for the one or more intelligent conversational agents to make a better decision criteria. In yet another embodiment of the present disclosure, the administrator of the mega-agent controller has ability to switch out the one or more intelligent conversational agents with minimal loss of data and intelligence. In yet another embodiment of the present disclosure, the administrator of the mega-agent controller has ability to perform A/B testing on the one or more intelligent conversational agents dynamically to see performance of the one or more intelligent conversational agents. In yet another embodiment of the present disclosure, the administrator of the mega-agent controller has cheaper costs of the one or more intelligent conversational agents. In yet another embodiment of the present disclosure, the administrator of the mega-agent controller has potential to trail out dead-end engagements in existing conversations.

In an embodiment of the present disclosure, the one or more vendors of the one or more intelligent conversational agents may provide anonymous centralized feedback on performance of the one or more intelligent conversational agents. In another embodiment of the present disclosure, the one or more vendors of the one or more intelligent conversational agents have ability to sell to a dedicated pool of user s and promote the one or more intelligent conversational agents.

The user/DMP module stores information and the first set of data associated with the plurality of users 302. The information of the plurality of users 302 stored is utilized to learn previous behavior. The user/DMP module segments the plurality of users 302 into groups and handles authentication of the plurality of users 302. The user/DMP module may improve engagement of the plurality of users 302. The user/DMP module stores known information of the plurality of users 302, profile of the plurality of users 302, behavior analysis of the plurality of users 302 and the like.

In an embodiment of the present disclosure, the user/DMP module performs authentication of the plurality of users 302. In another embodiment of the present disclosure, the user/DMP module creates profile of the plurality of users 302. In addition, the profile of the plurality of users 302 stores knowledge and summary of the plurality of users 302 over time. In yet another embodiment of the present disclosure, the user/DMP module includes defined roles for the plurality of users 302 and rules to guide the one or more intelligent conversational agents. In yet another embodiment of the present disclosure, the DMP module includes main data for the plurality of users 302. In addition, the DMP module provide statistics on the usage, engagements and recommendations in the chatbot switching system 202.

In an embodiment of the present disclosure, the chatbot switching system 202 has the ability to restrict information to be provided to the one or more intelligent conversational agents. In an example, an untrusted agent of the one or more intelligent conversational agents goes through appropriate security testing and audits before assigning the agent to the plurality of users 302. In addition, information or data is filtered based on the trusted agent or the untrusted agent. In an example, simple FAQ chatbot may not need to know full information or phone number of the plurality of users 302.

The profile in the user/DMP module is a simple structure such as a json or key-value pair that may be passed to the chatbot switching system 202. The one or more intelligent conversational agents are allowed to utilize the profile in the user/DMP module. The profile contains information. The information in the profile is split into known information, summarized information and inferred information. The known information includes information from social sites, Microsoft ads, surveys, third party CRM systems, and the like. The known information contains information such as age, gender, location, and the like.

The summarized information stores information that is part of the chatbot switching system 202. Each engagement from the one or more intelligent conversational agents have tags associated with them. Further, the tags are stored within the chatbot switching system 202. Furthermore, the tags are normalized by the mega-agent controller module. In an example, if user A is interested in pre-schools or cots, then profile of the user A is associated with an infant. In addition, summaries and counts are provided to the normalization engine to provide a holistic figure of profile of the user A. The tags are governed by a main platform. The tags need to be added under existing classification. In addition, the one or more vendors of the one or more intelligent conversational agents may also add taxonomy tags to the interest classification tree. The chatbot switching system 202 is able to determine inferred or additional information because of inferences of behavior of the plurality of users 302 within the chatbot switching system 202.

FIGS. 5A and 5B illustrate a flowchart 500 of a method for switching and handover between the one or more intelligent conversational agents, in accordance with various embodiments of the present disclosure. It may be noted that in order to explain the method of the flowchart 500, references will be made to the elements explained in FIG. 3. The flow chart 500 starts at step 502. At step 504, the chatbot switching system 202 receives the first set of data in real-time. At step 506, the chatbot switching system 202 collects the second set of data in real-time. At step 508, the chatbot switching system 202 fetches the one or more queries from the plurality of users 302 for the mega bot. At step 510, the chatbot switching system 202 analyzes the first set of data, the second set of data, and the one or more queries using the one or more machine learning algorithms. At step 512, the chatbot switching system 202 selects the suitable intelligent conversational agent from the one or more intelligent conversational agents having the trust score. At step 514, the chatbot switching system 202 switches between the one or more intelligent conversational agents in the mega bot.

The flow chart 500 terminates at step 516. It may be noted that the flowchart 500 is explained to have above stated process steps; however, those skilled in the art would appreciate that the flowchart 500 may have more/less number of process steps which may enable all the above stated embodiments of the present disclosure.

FIG. 6 illustrates a block diagram of a computing device 600, in accordance with various embodiments of the present disclosure. The computing device 600 includes a bus 602 that directly or indirectly couples the following devices: a memory 604, one or more processors 606, one or more presentation components 608, one or more input/output (I/O) ports 610, one or more input/output components 612, and an illustrative power supply 614. The bus 602 represents what may be one or more busses (such as an address bus, data bus, or combination thereof). Although the various blocks of FIG. 6 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventors recognize that such is the nature of the art, and reiterate that the diagram of FIG. 6 is merely illustrative of an exemplary computing device 600 that can be used in connection with one or more embodiments of the present invention. Distinction is not made between such categories as "workstation," "server," "laptop," "hand-held device," etc., as all are contemplated within the scope of FIG. 6 and reference to "computing device."

The computing device 600 typically includes a variety of computer-readable media. The computer-readable media can be any available media that can be accessed by the computing device 600 and includes both volatile and non-volatile media, removable and non-removable media. By way of example, and not limitation, the computer-readable media may comprise computer storage media and communication media. The computer storage media includes volatile and nonvolatile, removable and non-removable media implemented in any method or technology for storage of information such as computer-readable instructions, data structures, program modules or other data.

The computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computing device 600. The communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 604 includes computer-storage media in the form of volatile and/or nonvolatile memory. The memory 604 may be removable, non-removable, or a combination thereof. Exemplary hardware devices include solid-state memory, hard drives, optical-disc drives, etc. The computing device 600 includes one or more processors that read data from various entities such as memory 604 or I/O components 612. The one or more presentation components 608 present data indications to a user or other device. Exemplary presentation components include a display device, speaker, printing component, vibrating component, etc. The one or more I/O ports 610 allow the computing device 600 to be logically coupled to other devices including the one or more I/O components 612, some of which may be built in. Illustrative components include a microphone, joystick, game pad, satellite dish, scanner, printer, wireless device, etc.

The foregoing descriptions of specific embodiments of the present technology have been presented for purposes of illustration and description. They are not intended to be exhaustive or to limit the present technology to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is understood that various omissions and substitutions of equivalents are contemplated as circumstance may suggest or render expedient, but such are intended to cover the application or implementation without departing from the spirit or scope of the claims of the present technology.

While several possible embodiments of the invention have been described above and illustrated in some cases, it should be interpreted and understood as to have been presented only by way of illustration and example, but not by limitation. Thus, the breadth and scope of a preferred embodiment should not be limited by any of the above-described exemplary embodiments.

What is claimed:

1. A computer-implemented method for switching and handover between one or more intelligent conversational agents, the computer-implemented method comprising:

receiving, at a chatbot switching system with a processor, a first set of data in real-time, wherein the first set of data is associated with a plurality of users, wherein the first set of data comprising user behavioral information, past engagements with conversational agents and user profile information;

collecting, at the chatbot switching system with the processor, a second set of data in real-time, wherein the second set of data is associated with the one or more intelligent conversational agents, wherein the second set of data comprising a trust score associated with each of the one or more intelligent conversational agents, confidence level of the one or more intelligent conversational agents, past performance of the one or more intelligent conversational agents, and performance of each of the one or more intelligent conversational agents in a virtual environment;

fetching, at the chatbot switching system with the processor, one or more queries from the plurality of users for a mega bot, wherein the one or more queries are associated to a scope of field, wherein each of the one or more queries has a plurality of aspects, wherein the plurality of aspects comprising context, linguistic style, sentence construction, and lexical ambiguity;

analyzing, at the chatbot switching system with the processor, the first set of data, the second set of data and the one or more queries using one or more machine learning algorithms, wherein the analysis is performed based on training of a machine learning model, wherein the analysis is performed for enabling selection of a suitable intelligent conversational agent from the one or more intelligent conversational agents, wherein the analysis is performed in real time;

selecting, at the chatbot switching system with the processor, the suitable intelligent conversational agent from the one or more intelligent conversational agents having the trust score above a threshold level according to the plurality of aspects of each of the one or more queries, wherein the selection is based on the plurality of factors and the analysis of the first set of data, the second set of data and the one or more queries, wherein the mega bot selects the suitable intelligent conversational agent from the one or more intelligent conversational agents, wherein the threshold level is defined by an enterprise, wherein the plurality of factors comprising identification of the plurality of aspects, confidence level of the one or more intelligent conversational agents, past performance of the one or more intelligent conversational agents, behavior identification of the plurality of users, automated testing performance of the one or more intelligent conversational agents, performance of each of the one or more intelligent conversational agents in the virtual environment, cost of engagement with the one or more intelligent conversational agents and a feedback from the plurality of users;

creating, at the chatbot switching system with the processor, responses for the one or more queries using the suitable intelligent conversational agent from the one or more intelligent conversational agents;

creating a secondary response for the one or more queries in a virtual environment with a privacy rule limitation, wherein the privacy rule limitation corresponds to sharing the one or more queries with the one or more intelligent conversational agents not sharing the first set of data with the one or more intelligent conversational agents;

analyzing, at the chatbot switching system with the processor, the second response of the one or more intelligent conversational agents and improving the trust score of the one or more intelligent conversational agents based on the analysis of the second response; and switching, at the chatbot switching system with the processor, between the one or more intelligent conversational agents in the mega bot interacting with the plurality of users based on the plurality of aspects of corresponding query of the one or more queries and the plurality of factors.

2. The computer-implemented method as recited in claim 1, the chatbot switching system creates an online chatbot marketplace for enabling one or more vendors to upload the one or more intelligent conversational agents, wherein the online chatbot marketplace enables the enterprise to access the one or more intelligent conversational agents from the one or more vendors, wherein each of the one or more intelligent conversational agents is affiliated with the scope of field.

3. The computer-implemented method as recited in claim 1, further comprising integrating, at the chatbot switching system with the processor, the one or more intelligent conversational agents for generating the mega bot in real-time, wherein each of the one or more intelligent conversational agents has the trust score, wherein the trust score is dependent on the plurality of factors associated with the one or more intelligent conversational agents.

4. The computer-implemented method as recited in claim 1, further comprising computing, at the chatbot switching system with the processor, the trust score for each of the one or more intelligent conversational agents uploaded on the online chatbot marketplace by the one or more vendors, wherein the chatbot switching system ranks each of the one or more intelligent conversational agents in the online chatbot marketplace based on the trust score.

5. The computer-implemented method as recited in claim 1, further comprising receiving, at the chatbot switching system with the processor, the confidence level of the one or more intelligent conversational agents for responding to the one or more queries of the plurality of users, wherein each of the one or more intelligent conversational agents claims to have the confidence level to create response for the one or more queries.

6. The computer-implemented method as recited in claim 1, further comprising normalizing, at the chatbot switching system with the processor, the trust score of each of the one or more intelligent conversational agents based on each of the plurality of factors.

7. The computer-implemented method as recited in claim 1, further comprising predicting, at the chatbot switching system with the processor, journey of conversation between the plurality of users and the mega bot based on analysis performed on the first set of data, the second set of data, and the one or more queries using the one or more machine learning algorithms.

8. The computer-implemented method as recited in claim 1, further comprising detecting, at the chatbot switching system with the processor, the plurality of aspects associated with the one or more queries using the machine learning model in real-time.

9. The computer-implemented method as recited in claim 1, further comprising determining, at the chatbot switching system with the processor, transition of the plurality of aspects within the conversation between the plurality of users and the mega bot based on analysis performed on the one or more queries using the one or more machine learning algorithms, wherein the determination of the transition of the plurality of aspects within the conversation enables the chatbot switching system to switch between the one or more intelligent conversational agents in the mega bot interacting with the plurality of users.

10. A computer system comprising:
one or more processors; and
a memory coupled to the one or more processors, the memory for storing instructions which, when executed by the one or more processors, cause the one or more processors to perform a method for switching and handover between one or more intelligent conversational agents, the method comprising:
receiving, at a chatbot switching system, a first set of data in real-time, wherein the first set of data is associated with a plurality of users, wherein the first set of data comprising user behavioral information, past engagements with conversational agents and user profile information;
collecting, at the chatbot switching system, a second set of data in real-time, wherein the second set of data is associated with the one or more intelligent conversational agents, wherein the second set of data comprising a trust score associated with each of the one or more intelligent conversational agents, confidence level of the one or more intelligent conversational agents, past performance of the one or more intelligent conversational agents, and performance of each of the one or more intelligent conversational agents in a virtual environment;
fetching, at the chatbot switching system, one or more queries from the plurality of users for a mega bot, wherein the one or more queries are associated to a scope of field, wherein each of the one or more queries has a plurality of aspects, wherein the plurality of aspects comprising context, linguistic style, sentence construction, and lexical ambiguity;
analyzing, at the chatbot switching system, the first set of data, the second set of data and the one or more queries using one or more machine learning algorithms, wherein the analysis is performed based on training of a machine learning model, wherein the analysis is performed for enabling selection of a suitable intelligent conversational agent from the one or more intelligent conversational agents, wherein the analysis is performed in real time;
selecting, at the chatbot switching system, the suitable intelligent conversational agent from the one or more intelligent conversational agents having the trust score above a threshold level according to the plurality of aspects of each of the one or more queries, wherein the selection is based on the plurality of factors and the analysis of the first set of data, the second set of data and the one or more queries, wherein the mega bot selects the suitable intelligent conversational agent from the one or more intelligent conversational agents, wherein the threshold level is defined by an enterprise, wherein the plurality of factors comprising identification of the plurality of aspects, confidence level of the one or more intelligent conversational agents, past performance of the one or more intelligent conversational agents, behavior identification of the plurality of users, automated testing performance of the one or more intelligent conversational agents, performance of each of the one or more intelligent conversational agents in the virtual environment, cost of engagement with the one or more intelligent conversational agents and a feedback from the plurality of users;
creating, at the chatbot switching system with the processor, responses for the one or more queries using the suitable intelligent conversational agent from the one or more intelligent conversational agents;
creating a secondary response for the one or more queries in a virtual environment with a privacy rule limitation, wherein the privacy rule limitation corresponds to sharing the one or more queries with the one or more intelligent conversational agents not sharing the first set of data with the one or more intelligent conversational agents;
analyzing, at the chatbot switching system with the processor, the second response of the one or more intelligent conversational agents and improving the trust score of the one or more intelligent conversational agents based on the analysis of the second response; and
switching, at the chatbot switching system, between the one or more intelligent conversational agents in the mega bot interacting with the plurality of users based on the plurality of aspects of corresponding query of the one or more queries and the plurality of factors.

11. The computer system as recited in claim 10, wherein the chatbot switching system creates an online chatbot marketplace for enabling one or more vendors to upload the one or more intelligent conversational agents, wherein the online chatbot marketplace enables the enterprise to access the one or more intelligent conversational agents from the one or more vendors, wherein each of the one or more intelligent conversational agents is affiliated with the scope of field.

12. The computer system as recited in claim 10, further comprising integrating, at the chatbot switching system, the one or more intelligent conversational agents for generating the mega bot in real-time, wherein each of the one or more intelligent conversational agents has the trust score, wherein the trust score is dependent on the plurality of factors associated with the one or more intelligent conversational agents.

13. The computer system as recited in claim 10, further comprising computing, at the chatbot switching system, the trust score for each of the one or more intelligent conversational agents uploaded on the online chatbot marketplace by the one or more vendors, wherein the chatbot switching system ranks each of the one or more intelligent conversational agents in the online chatbot marketplace based on the trust score.

14. The computer system as recited in claim 10, further comprising receiving, at the chatbot switching system, the confidence level of the one or more intelligent conversational agents for responding to the one or more queries of the plurality of users, wherein each of the one or more intelligent conversational agents claims to have the confidence level to create response for the one or more queries.

15. The computer system as recited in claim 10, further comprising normalizing, at the chatbot switching system, the trust score of each of the one or more intelligent conversational agents based on each of the plurality of factors.

16. The computer system as recited in claim 10, further comprising predicting, at the chatbot switching system, journey of conversation between the plurality of users and the mega bot based on analysis performed on the first set of data, the second set of data, and the one or more queries using the one or more machine learning algorithms.

17. The computer system as recited in claim 10, further comprising detecting, at the chatbot switching system, the plurality of aspects associated with the one or more queries using the machine learning model in real-time.

18. The computer system as recited in claim 10, further comprising determining, at the chatbot switching system, transition of the plurality of aspects within the conversation between the plurality of users and the mega bot based on analysis performed on the one or more queries using the one or more machine learning algorithms, wherein the determination of the transition of the plurality of aspects within the conversation enables the chatbot switching system to switch between the one or more intelligent conversational agents in the mega bot interacting with the plurality of users.

19. A non-transitory computer-readable storage medium encoding computer executable instructions that, when executed by at least one processor, performs a method for switching and handover between one or more intelligent conversational agents, the method comprising:
  receiving, at a computing device, a first set of data in real-time, wherein the first set of data is associated with a plurality of users, wherein the first set of data comprising user behavioral information, past engagements with conversational agents and user profile information;
  collecting, at the computing device, a second set of data in real-time, wherein the second set of data is associated with the one or more intelligent conversational agents, wherein the second set of data comprising a trust score associated with each of the one or more intelligent conversational agents, confidence level of the one or more intelligent conversational agents, past performance of the one or more intelligent conversational agents, and performance of each of the one or more intelligent conversational agents in a virtual environment;
  fetching, at the computing device, one or more queries from the plurality of users for a mega bot, wherein the one or more queries are associated to a scope of field, wherein each of the one or more queries has a plurality of aspects, wherein the plurality of aspects comprising context, linguistic style, sentence construction, and lexical ambiguity;
  analyzing, at the computing device, the first set of data, the second set of data and the one or more queries using one or more machine learning algorithms, wherein the analysis is performed based on training of a machine learning model, wherein the analysis is performed for enabling selection of a suitable intelligent conversational agent from the one or more intelligent conversational agents, wherein the analysis is performed in real time;
  selecting, at the computing device, the suitable intelligent conversational agent from the one or more intelligent conversational agents having the trust score above a threshold level according to the plurality of aspects of each of the one or more queries, wherein the selection is based on the plurality of factors and the analysis of the first set of data, the second set of data and the one or more queries, wherein the mega bot selects the suitable intelligent conversational agent from the one or more intelligent conversational agents, wherein the threshold level is defined by an enterprise, wherein the plurality of factors comprising identification of the plurality of aspects, confidence level of the one or more intelligent conversational agents, past performance of the one or more intelligent conversational agents, behavior identification of the plurality of users, automated testing performance of the one or more intelligent conversational agents, performance of each of the one or more intelligent conversational agents in the virtual environment, cost of engagement with the one or more intelligent conversational agents and a feedback from the plurality of users;
  creating, at the chatbot switching system with the processor, responses for the one or more queries using the suitable intelligent conversational agent from the one or more intelligent conversational agents;
  creating a secondary response for the one or more queries in a virtual environment with a privacy rule limitation, wherein the privacy rule limitation corresponds to sharing the one or more queries with the one or more intelligent conversational agents not sharing the first set of data with the one or more intelligent conversational agents;
  analyzing, at the chatbot switching system with the processor, the second response of the one or more intelligent conversational agents and improving the trust score of the one or more intelligent conversational agents based on the analysis of the second response; and
  switching, at the computing device, between the one or more intelligent conversational agents in the mega bot interacting with the plurality of users based on the plurality of aspects of corresponding query of the one or more queries and the plurality of factors.

* * * * *